US006486350B1

(12) United States Patent
Audia et al.

(10) Patent No.: US 6,486,350 B1
(45) Date of Patent: Nov. 26, 2002

(54) BIOLOGICAL REAGENTS AND METHODS FOR DETERMINING THE MECHANISM IN THE GENERATION OF β-AMYLOID PEPTIDE

(75) Inventors: James E. Audia, Indianapolis, IN (US); Paul A. Hyslop, Indianapolis, IN (US); Jeffrey S. Nissen, Indianapolis, IN (US); Richard C. Thompson, Frankfort, IN (US); Jay S. Tung, Belmont, CA (US); Laura I. Tanner, San Francisco, CA (US)

(73) Assignees: Elan Pharmaceuticals Inc., So. San Francisco, CA (US); Eli Lilly & Company, Indianapolis, IN (US)

( * ) Notice: Subject to any disclaimer, the term of this patent is extended or adjusted under 35 U.S.C. 154(b) by 0 days.

(21) Appl. No.: 09/408,283

(22) Filed: Sep. 29, 1999

Related U.S. Application Data
(60) Provisional application No. 60/160,082, filed on Sep. 30, 1998, now abandoned.

(51) Int. Cl.[7] ............................................. C07C 233/05
(52) U.S. Cl. ........................... 564/153; 560/25; 560/27; 560/29; 540/522
(58) Field of Search ............................ 564/153; 560/25, 560/27, 29; 540/522

(56) References Cited

U.S. PATENT DOCUMENTS 4,666,829 A    5/1987   Glenner et al.

FOREIGN PATENT DOCUMENTS

| EP | 0293170 A | 11/1988 |
|---|---|---|
| WO | WO 91/13904 | 9/1991 |
| WO | WO 93/04194 | 3/1993 |
| WO | WO 98/22430 | 5/1998 |
| WO | WO 98/22441 | 5/1998 |
| WO | WO 98/22493 | 5/1998 |
| WO | WO98/22494 | 5/1998 |
| WO | WO 98/22949 | 5/1998 |
| WO | WO 98/28268 | 10/1998 |

OTHER PUBLICATIONS

Chartier–Harlan, et al., "Early–Onset Alzheimer's Disease Caused by Mutations at Codon 717 of the β–Amyloid Precursor Protein Gene", Nature, 353:844–846 (1989).
Glenner, et al., "Alzheimer's Disease: Initial Report of the Purification and Characterization of a Novel Cerebrovascular Amyloid Protein", Biochem. Biophys. Res. Commun., 120:885–890 (1984).

Goate, et al., "Segregation of a Missense Mutation in the Amyloid Precursor Protein Gene with Familial Alzheimer's Disease", Nature, 349:704–706 (1990).
Jin, et al., "Pettides Containing the RERMS Sequence of Amyloid β/A4 Protein Precursor Bind Cell Surface and Promote Neurite Extension", J Neuroscience 14(9):5461–5470 (1994).
Mullan, et al., A Pathogenic Mutation for Probable Alzheimer's Disease in the APP Gene at the N–Terminus of β–Amyloid, Nature Genet., 1:345–347 (1992).
Mundy, Dorthy I., "Identification of the Multicalytic Enzyme as a possible γ–Secretase for the Amyloid Precursor Protein", Biochem.Biophys.Res.Comm., 204(1):333–341 (1994).
Murrell, et al., "A Mutation in the Amyloid Precursor Protein Associated with Hereditary Alzheimer's Disease", Science, 254:97–99 (1991).
Roy, et al., "Synthesis of New Polymerizable Metal–Chelating Lipids", J. Org. Chem. 64:2969–2974 (1999).
Selkoe, "The Molecular Pathology of Alzheimer's Disease", Neuron, 6:487–498 (1991).
Sigal, et al., "Polyacrylamides Bearing Pendant α–Sialoside Groups Strongly Inhibit Agglutination of Erythrocytes of Influenza Virus: The Strong Inhibition Reflects Enhanced Binding throuhg Cooperative Polyvalent Interactions", Amer. Chem. Soc., 118(16):3789–3800 (1996).
Weber, et al., "Enhanced Kidney Clearance with an Ester–Linked $^{99m}$Tc–Radiolabeled Antibody Fab'—Chelator Conjugate", Bioconjugate Chem., 1(6) 431–437 (1990).
Garrigues, Bernard, et al., "Synthesis of Spermine and Spermidine Selectively Substituted On The Secondary Amine Functions," Bull. Soc. Chim. Belg., 97(10):775–785 (1988).
T. J. Norman, et al., "Towards Selective DNA Targeting: Synthesis of an Antibody–Macrocyle–Intercalator Conjugate," Journal of the Chemical Society, Chemical Communications:1879–1880 (1995).
S. Hashimoto, et al., "Synthesis of Bis(N–Methylpyrrole Oligopeptide–Linked Hydroxamic Acids) And Effective DNA Cleavage By Their Vanadyl Complexes," Heterocycles, vol. 48, No. 5:939–947 (1998).

Primary Examiner—Shailendra Kumar
(74) Attorney, Agent, or Firm—Burns, Doane, Doane, Swecker & Mathis LLP

(57) ABSTRACT

Disclosed are biological reagents which comprise compounds that inhibit β-amyloid peptide release and/or its synthesis, and, accordingly, have utility in determining the cellular mechanism involved in the generation of β-amyloid peptide.

2 Claims, No Drawings

BIOLOGICAL REAGENTS AND METHODS FOR DETERMINING THE MECHANISM IN THE GENERATION OF β-AMYLOID PEPTIDE

This application claims the benefit of No. 60/160,082, filed Sep. 30, 1998 now abandoned.

BACKGROUND OF THE INVENTION

FIELD OF THE INVENTION

This invention relates to biological reagents which comprise compounds that inhibit β-amyloid peptide release and/or its synthesis, and, accordingly, have utility in determining the cellular mechanism involved in the generation of β-amyloid peptide.

REFERENCES

The following publications, patents and patent applications are cited in this application as superscript numbers:

[1] Glenner, et al., "Alzheimer's Disease: Initial Report of the Purification and Characterization of a Novel Cerebrovascular Amyloid Protein", Biochem. Biophys. Res. Commun., 120:885–890 (1984).

[2] Glenner, et al., "Polypeptide Marker for Alzheimer's Disease and its Use for Diagnosis", U.S. Pat. No. 4,666,829 issued May 19, 1987.

[3] Selkoe, "The Molecular Pathology of Alzheimer's Disease", Neuron, 6:487–498 (1991).

[4] Goate, et al., "Segregation of a Missense Mutation in the Amyloid Precursor Protein Gene with Familial Alzheimer's Disease", Nature, 349:704–706 (1990).

[5] Chartier-Harlan, et al., "Early-Onset Alzheimer's Disease Caused by Mutations at Codon 717 of the β-Amyloid Precursor Proteing Gene", Nature, 353:844–846 (1989).

[6] Murrell, et al., "A Mutation in the Amyloid Precursor Protein Associated with Hereditary Alzheimer's Disease", Science, 254:97–99 (1991).

[7] Mullan, et al., "A Pathogenic Mutation for Probable Alzheimer's Disease in the APP Gene at the N-Terminus of β-Amyloid, Nature Genet., 1:345–347 (1992).

[8] International Patent Application No. PCT/US97/20356; Publication No. WO98/22441

[9] International Patent Application No. PCT/US97/20355; Publication No. WO98/22430

[10] International Patent Application No. PCT/US97/18704; Publication No. WO98/22493

[11] International Patent Application No. PCT/US97/20804; Publication No. WO98/22494

[12] Bioconjugate Chemistry (1990) 1(6) 431–437

[13] International Patent Application No. PCT/US97/22986; Publication No. WO98/28268

All of the above publications, patents and patent applications are herein incorporated by reference in their entirety to the same extent as if each individual publication, patent or patent application was specifically and individually indicated to be incorporated by reference in its entirety.

STATE OF THE ART

Alzheimer's Disease (AD) is a degenerative brain disorder characterized clinically by progressive loss of memory, cognition, reasoning, judgment and emotional stability that gradually leads to profound mental deterioration and ultimately death. AD is a very common cause of progressive mental failure (dementia) in aged humans and is believed to represent the fourth most common medical cause of death in the United States. AD has been observed in races and ethnic groups worldwide and presents a major present and future public health problem. The disease is currently estimated to affect about two to three million individuals in the United States alone. AD is at present incurable. No treatment that effectively prevents AD or reverses its symptoms and course is currently known.

The brains of individuals with AD exhibit characteristic lesions termed senile (or amyloid) plaques, amyloid angiopathy (amyloid deposits in blood vessels) and neurofibrillary tangles. Large numbers of these lesions, particularly amyloid plaques and neurofibrillary tangles, are generally found in several areas of the human brain important for memory and cognitive function in patients with AD. Smaller numbers of these lesions in a more restrictive anatomical distribution are also found in the brains of most aged humans who do not have clinical AD. Amyloid plaques and amyloid angiopathy also characterize the brains of individuals with Trisomy 21 (Down's Syndrome) and Hereditary Cerebral Hemorrhage with Amyloidosis of the Dutch Type (HCHWA-D). At present, a definitive diagnosis of AD usually requires observing the aforementioned lesions in the brain tissue of patients who have died with the disease or, rarely, in small biopsied samples of brain tissue taken during an invasive neurosurgical procedure.

The principal chemical constituent of the amyloid plaques and vascular amyloid deposits (amyloid angiopathy) characteristic of AD and the other disorders mentioned above is an approximately 4.2 kilodalton (kD) protein of about 39–43 amino acids designated the β-amyloid peptide (βAP) or sometimes Aβ, AβP or β/A4. β-Amyloid peptide was first purified and a partial amino acid sequence was provided by Glenner, et al.[1] The isolation procedure and the sequence data for the first 28 amino acids are described in U.S. Pat. No. 4,666,829[2].

Molecular biological and protein chemical analyses have shown that the β-amyloid peptide is a small fragment of a much larger precursor protein (APP), that is normally produced by cells in many tissues of various animals, including humans. Knowledge of the structure of the gene encoding the APP has demonstrated that β-amyloid peptide arises as a peptide fragment that is cleaved from APP by protease enzymes. The precise biochemical mechanism by which the β-amyloid peptide fragment is cleaved from APP and subsequently deposited as amyloid plaques in the cerebral tissue and in the walls of the cerebral and meningeal blood vessels is currently unknown.

Several lines of evidence indicate that progressive cerebral deposition of β-amyloid peptide plays a seminal role in the pathogenesis of AD and can precede cognitive symptoms by years or decades. See, for example, Selkoe[3]. The most important line of evidence is the discovery that missense DNA mutations at amino acid 717 of the 770-amino acid isoform of APP can be found in affected members but not unaffected members of several families with a genetically determined (familial) form of AD (Goate, et al.[4]; Chartier Harlan, et al.[5]; and Murrell, et al.[6]) and is referred to as the Swedish variant. A double mutation changing lysine[595]-methionine[596] to asparagine[595]-leucine[596] (with reference to the 695 isoform) found in a Swedish family was reported in 1992 (Mullan, et al.[7]). Genetic linkage analyses have demonstrated that these mutations, as well as certain other mutations in the APP gene, are the specific molecular cause of AD in the affected members of such families. In addition, a mutation at amino acid 693 of the 770-amino acid isoform of APP has been identified as the cause of the β-amyloid peptide deposition disease, HCHWA-D, and a change from alanine to glycine at amino acid 692 appears to cause a phenotype that resembles AD is some patients but HCHWA-D in others. The discovery of these and other mutations in APP in genetically based cases of AD prove that alteration of APP and subsequent deposition of its β-amyloid peptide fragment can cause AD.

Despite the progress which has been made in understanding the underlying mechanisms of AD and other β-amyloid peptide related diseases, there still remains a need to determine the precise mechanism for the generation of β-amyloid peptide. Biological reagents comprising compounds known to inhibit the generation of β-amyloid peptide would be useful in determining the mechanism for the generation of β-amyloid peptide and thus AD. Knowledge of the disease mechanism would, in turn, allow rationale drug design of novel entities which specifically target AD.

SUMMARY OF THE INVENTION

This invention is directed to the discovery of a class of biological reagents which comprise compounds that inhibit β-amyloid peptide release and/or its synthesis and, therefore, are useful in determining the underlying cellular mechanism leading to AD in patients susceptible to AD. The class of biological reagents having the described properties are defined by formula I below:

A—B—C     I wherein:

A is selected from the group consisting of formulas II, III, IV and V below;

B is selected from the group consisting of
  a) $(CH_2CH(R)Q)_n$ 
  b) alkylene-Q
  c) substituted alkylene-Q
     wherein R is selected from hydrogen, alkyl, aryl and Q is selected from the group consisting of —O—, —S—, —NH—, —OC(O)NH—, —NHC(O)O—, —NHC(O)NH—, —NHC(O)— and —C(O)NH—; and C is selected from the group consisting of a solid support and a detectable marker wherein C is optionally linked to Q through a linking arm;

wherein Formula II is defined as follows:

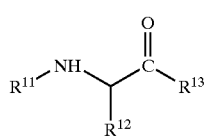

wherein $R^{11}$ is selected from the group consisting of:

(a) a substituted phenyl group of the formula:

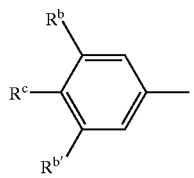

wherein
  $R^c$ is selected from the group consisting of acyl, alkyl, alkoxy, alkoxycarbonyl, alkylalkoxy, azido, cyano, halo, hydrogen, nitro, trihalomethyl, thioalkoxy, and wherein $R^b$ and $R^c$ are fused to form a heteroaryl or heterocyclic ring with the phenyl ring wherein the heteroaryl or heterocyclic ring contains from 3 to 8 atoms of which from 1 to 3 are heteroatoms independently selected from the group consisting of oxygen, nitrogen and sulfur;
  $R^b$ and $R^{b'}$ are independently selected from the group consisting of hydrogen, halo, nitro, cyano, trihalomethyl, alkoxy, and thioalkoxy with the proviso that $R^b$, $R^{b'}$ and $R^c$ are not all hydrogen and with the further proviso that when $R^c$ is hydrogen, then neither $R^b$ nor $R^{b'}$ are hydrogen;
(b) 2-naphthyl; and
(c) 2-naphthyl substituted at the 4, 5, 6, 7 and/or 8 positions with 1 to 5 substituents selected from the group consisting of alkyl, alkoxy, halo, cyano, nitro, trihalomethyl, and thioalkoxy;

$R^{12}$ is selected from the group consisting of hydrogen, alkyl of from 1 to 4 carbon atoms, alkylalkoxy of from 1 to 4 carbon atoms and alkylthioalkoxy of from 1 to 4 carbon atoms; and $R^{13}$ is selected from the group consisting of —O—, —S—, —O—$(CH_2)_pC(O)$—, —O—$(CH_2)_pC(O)O$— and —O—$(CH_2)_pC(O)NH$—, wherein p is an integer of from 1 to 2;

wherein Formula III is defined as follows:

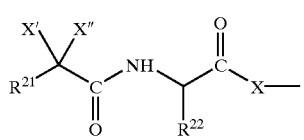

wherein $R^{21}$ is selected from the group consisting of
  a) alkyl, alkenyl, alkcycloalkyl, phenyl-$(R^d)_m$-, naphthyl-$(R^d)_m$- wherein $R^d$ is an alkylene group of from 1 to 8 carbon atoms and m is an integer equal to 0 or 1, cycloalkyl, cycloalkenyl, 3-pyridyl, 4-pyridyl and heteroaryl, other than 3- and 4-pyridyl, of 3 to 10 atoms and 1 to 4 heteroatoms selected from oxygen, sulfur and nitrogen wherein the heteroaryl group is optionally substituted with 1 to 3 substituents selected from the group consisting of alkyl, alkoxy, aryl, aryloxy, halo, nitro, thioalkoxy, and thioaryloxy with the proviso that for such heteroaryls when there is at least one nitrogen heteroatom, there is also at least one oxygen and/or sulfur heteroatom;

(b) a substituted phenyl group of the formula:

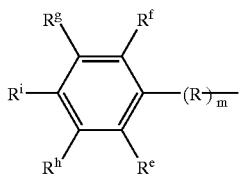

wherein
R is alkylene of from 1 to 8 carbon atoms,
m is an integer equal to 0 or 1,
$R^e$ and $R^f$ are independently selected from the group consisting of hydrogen, hydroxy, fluoro and methyl;
$R^g$ and $R^h$ are independently selected from the group consisting of hydrogen, alkyl, alkoxy, aryl, cyano, cycloalkyl, halo, heteroaryl, heterocyclic, nitro, trihalomethyl, thioalkoxy, thioaryloxy, thioheteroaryloxy, and —C(O)$R^j$ where $R^j$ is selected from the group consisting of alkyl, aryl, alkoxy and aryloxy; and
$R^i$ is selected from the group consisting of hydrogen, alkyl, aryl, cyano, halo, nitro, and where $R^g$ and $R^i$ are fused to form a methylenedioxy ring with the phenyl ring; and
when $R^g$ and/or $R^h$ and/or $R^i$ is fluoro, chloro, bromo and/or nitro, then $R^e$ and/or $R^f$ can also be chloro; and
(c) 1- or 2-naphthyl-$(R^k)_m$-substituted at the 5, 6, 7 and/or 8 positions with 1 to 4 substituents selected from the group consisting alkyl, alkoxy, halo, cyano, nitro, trihalomethyl, and thioalkoxy wherein $R^k$ is an alkylene group of from 1 to 8 carbon atoms and m is an integer equal to 0 or 1;
$R^{22}$ is selected from the group consisting of hydrogen, alkyl, phenyl, alkylalkoxy, alkylthioalkoxy;
X is oxygen or sulfur;
X' is hydrogen, hydroxy or fluoro; and
X" is hydrogen, hydroxy or fluoro, or X' and X" together form an oxo group;
wherein Formula IV is defined as follows:

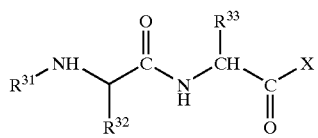

wherein:
$R^{31}$ is selected from the group consisting of
(a) phenyl,
(b) a substituted phenyl group of the formula:

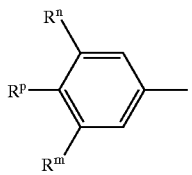

wherein
$R^p$ is selected from the group consisting of acyl, alkyl, alkoxy, alkylalkoxy, azido, cyano, halo, hydrogen, nitro, trihalomethyl, thioalkoxy, and wherein $R^p$ and $R^m$ are fused to form a heteroaryl or heterocyclic ring with the phenyl ring,
$R^m$ and $R^n$ are independently selected from the group consisting of hydrogen, halo, nitro, cyano, trihalomethyl, alkoxy, and thioalkoxy with the proviso that when $R^p$ is hydrogen, then $R^m$ and $R^n$ are either both hydrogen or both substituents other than hydrogen,
(c) 2-naphthyl,
(d) 2-naphthyl substituted at the 4, 5, 6, 7 and/or 8 positions with 1 to 5 substituents selected from the group consisting of alkyl, alkoxy, halo, cyano, nitro, trihalomethyl, thioalkoxy, aryl, and heteroaryl,
(e) heteroaryl, and
(f) substituted heteroaryl containing 1 to 3 substituents selected from the group consisting of alkyl, alkoxy, aryl, aryloxy, cyano, halo, nitro, heteroaryl, thioalkoxy and thioaryloxy provided that said substituents are not ortho (adjacent) to the heteroaryl attachment to the —NH group;
$R^{32}$ is selected from the group consisting of hydrogen, alkyl of from 1 to 4 carbon atoms, alkylalkoxy of from 1 to 4 carbon atoms, alkylthioalkoxy of from 1 to 4 carbon atoms, aryl, heteroaryl, substituted aryl and substituted heteroaryl provided that the substituents are not ortho (adjacent) to the attachment of the aryl or heteroaryl atom to the carbon atom;
$R^{33}$ is selected from the group consisting of alkyl, alkenyl, alkynyl, aryl, cycloalkyl, cycloalkenyl, heteroaryl, substituted alkyl, substituted alkenyl, substituted alkynyl, and heterocyclic; and
X is selected from the group consisting of oxygen and sulfur; and
wherein Formula V is defined as follows:

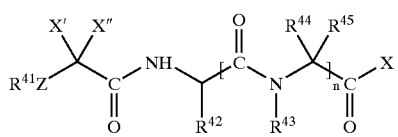

wherein
$R^{41}$ is selected from the group consisting of alkyl, alkenyl, alkynyl, cycloalkyl, cycloalkenyl, substituted alkyl, substituted alkenyl, substituted alkynyl, aryl, heteroaryl and heterocyclic;
$R^{42}$ is selected from the group consisting of hydrogen, alkyl, substituted alkyl, alkenyl, substituted alkenyl, alkynyl, substituted alkynyl, cycloalkyl, aryl, heteroaryl and heterocyclic;
each $R^{43}$ is independently selected from the group consisting of hydrogen and methyl and $R^{43}$ together with $R^{44}$ can be fused to form a cyclic structure of from 3 to 8 atoms which is optionally fused with an aryl or heteroaryl group;
each $R^{44}$ is independently selected from the group consisting of hydrogen, alkyl, alkenyl, alkynyl, aryl, cycloalkyl, cycloalkenyl, heteroaryl, heterocyclic, substituted alkyl, substituted alkenyl and substituted alkynyl;
each $R^{45}$ is selected from hydrogen and methyl or together with $R^{43}$ forms a cycloalkyl group of from 3 to 6 carbon atoms;
X is selected from oxygen, sulfur and NH;

X' is hydrogen, hydroxy or fluoro; and

X" is hydrogen, hydroxy or fluoro, or X' and X" together form an oxo group;

Z is selected from the group consisting of a bond covalently linking $R^{41}$ to —CX'X"—, oxygen and sulfur; and n is an integer equal to 1 to 3;

wherein the compounds of formulas II, III, IV and V are effective in inhibiting the cellular release and/or synthesis of β-amyloid peptide.

Accordingly, in one of its method aspects, this invention is directed to a method for determining the proteins involved in β-amyloid peptide release and/or its synthesis in a cell which method comprises contacting the components of a cell with an effective amount of a biological reagent or a mixture of biological reagents of formula I above.

In another of its composition aspects, this invention is directed to intermediates useful in the synthesis of compounds of formula I wherein said intermediates are represented by formula VI

A—B'  VI wherein:

A is selected from the group consisting of formulas II, III, IV and V as described above; and B' is selected from the group consisting of
  a) $(CH_2CH(R)Q)_nH$
  b) alkylene-Q-H
  c) substituted alkylene-Q-H
    wherein R is selected from hydrogen, alkyl, aryl and Q is selected from the group consisting of —O—, —S—, —NH—.

Suitable compounds described by formula I and VI above include, by way of example, the following:

Tert-butyl N-(8-amino-3,6-dioxaoctyl) carbamate
Methyl N-2-aminoethyl-N'-2-t-butylcarbamoylethyl amine
Tert-butyl N-(8-N'-(N"-benzyloxycarbonyl-L-phenylglycine)-3,6-dioxaoctyl) carbamate
Methyl N-(2-N'-(N"-benzyloxycarbamoyl-L-phenylglycine) ethyl)-N'-2-t-butylcarbamoylethyl amine
Tert-butyl N-(2-N'-(N"-benzyloxycarbonyl-L-phenylglycine)-ethyl) carbamate
Tert-butyl N-(8-N'L-phenylglycine-3,6-dioxaoctyl) carbamate
Methyl N-(2-N-(L-phenylglycine)ethyl)-N'-2-t-butylcarbamoylethyl amine
Tert-butyl N-(2-N'-L-phenylglycine)-ethyl carbamate
Tert-butyl N-[8-N'-((2-(R/S)-hydroxy-2-(3,5-difluorophenyl)-acetyl-L-alaninyl)-L-phenylglycine)-3,6-dioxaoctyl] carbamate
Methyl N-[2-N-((2-(R/S)-hydroxy-2-(3,5-difluorophenyl)-acetyl-L-alaninyl)-L-phenylglycine)ethyl]-N'-2-t-butylcarbamoylethyl amine
Tert-butyl N-[2-N'-((2-(R/S)-hydroxy-2-(3,5-difluorophenyl)-acetyl-L-alaninyl)-L-phenylglycine)-ethyl]carbamate
Tert-butyl-2-(2'-(N'-benzyloxycarbonyl-L-phenylglycine) aminoethoxy)ethylcarbamate
Tert-butyl-2-(2'-(L-phenylglycine)aminoethoxy) ethylcarbamate.
N-((R/S)-3,5-difluorophenyl-α-hydroxyacetyl)-L-alanine, methyl ester
N-((R/S-3,5-difluorophenyl-α-hydroxyacetyl)-L-alanine
Tert-butyl-2-(2'-(N'-(((R/S)-3,5-difluorophenyl-α-hydroxyacetyl)-L-alanine)-L-phenylglycine) aminoethoxy)ethylcarbamate
8-N'-((2-(R/S)-hydroxy-2-(3,5-difluorophenyl)-acetyl-L-alaninyl)-L-phenylglycinyl)amino-3,6-dioxaoctylamine hydrochloride
Methyl N-[2-N-((2-(R/S)-hydroxy-2-(3,5-difluorophenyl)-acetyl-L-alaninyl)-L-phenylglycinyl)aminoethyl]-N'-2-aminoethyl amine hydrochloride
2-N'-((2-(R/S)-hydroxy-2-(3,5-difluorophenyl)-acetyl-L-alaninyl)-L-phenylglycine)-ethylamine hydrochloride
N-(8-N'-((2-(R/S)-hydroxy-2-(3,5-difluorophenyl)-acetyl-L-alaninyl)-L-phenylglycine)-3,6-dioxaoctyl)-biotinamide
2-(2'-(N'-(((R/S)-3,5-difluorophenyl-α-hydroxyacetyl)-L-alanine)-L-phenylglycine)aminoethoxy)ethylamine, hydrochloride salt
1-[N-(3,5-difluorophenylacetyl)-L-alaninyl)-(L-phenylglycinyl)]amino-6-(N-biotinyl)aminohexane
1-[N-(3,5-difluorophenylacetyl)-L-alaninyl)-(L-phenylglycinyl)]amino-3-(4-iodophenoxy)propane
1-[N-(3,5-difluorophenylacetyl)-L-alaninyl)-(L-phenylglycinyl)]amino-6-[N-(4-amino-7-nitrobenzofurazanyl)]hexane
1-[N-(3,5-difluorophenylacetyl)-L-alaninyl)-(L-phenylglycinyl)]amino-3-(4-trimethylstannylphenoxy) propane
N-{1-N-[N-(3,5-difluorophenylacetyl)-L-alaninyl-(L-phenylglycinyl)amino-6-hexyl]}-4,4-difluoro-5,7-dimethyl-4-bora-3α,4α-diaza-s-indacene-3-propionamide
N-{methyl N-[2-N-((2-(R/S)-hydroxy-2-(3,5-difluorophenyl)-acetyl-L-alaninyl)-L-phenylglycinyl) aminoethyl]-N'-2-aminoethyl}-4,4-difluoro-5,7-dimethyl-4-bora-3α,4α-diaza-s-indacene-3-propionamide
N-[8-N'-((2-(R/S)-hydroxy-2-(3,5-difluorophenyl)-acetyl-L-alaninyl)-L-phenylglycinyl)amino-3,6-dioxaoctyl]-4,4-difluoro-5,7-dimethyl-4-bora-, 3α,4α-diaza-s-indacene-3-propionamide
5-(S)-[N'-((S)-3,5-Difluorophenyl-α-hydroxyacetyl)-L-alaninyl]amino-7-methyl-5,7-dihydro-6H-dibenz[b,d] azepin-6-one
5-(S)-[N'-((R)-3,5-Difluorophenyl-α-hydroxyacetyl)-L-alaninyl]amino-7-methyl-5,7-dihydro-6H-dibenz[b,d] azepin-6-one
5-(S)-(N'-((S)-(+)-2-Hydroxy-3-methylbutyryl)-L-alaninyl) amino-7-methyl-5,7-dihydro-6H-dibenz[b,d]azepin-6-one
1-[N-(3,5-difluorophenylacetyl)-L-alaninyl)-(L-phenylglycinyl)]amino-4-p-azidosalicylamidobutane

DETAILED DESCRIPTION OF THE INVENTION

As above, this invention relates to biological reagents comprising compounds which inhibit β-amyloid peptide release and/or its synthesis, and, accordingly, have utility in determining the mechanism for the generation of β-amyloid peptide. However, prior to describing this invention in further detail, the following terms will first be defined.

Definitions

The term "β-amyloid peptide" refers to a 39–43 amino acid peptide having a molecular weight of about 4.2 kD, which peptide is substantially homologous to the form of the protein described by Glenner, et al.[1] including mutations and post-translational modifications of the normal β-amyloid peptide. In whatever form, the β-amyloid peptide is approximately a 39–43 amino acid fragment of a large membrane-spanning glycoprotein, referred to as the β-amyloid precursor protein (APP). Its 43-amino acid sequence is:

1
Asp Ala Glu Phe Arg His Asp Ser Gly Tyr
11
Glu Val His His Gln Lys Leu Val Phe Phe
21
Ala Glu Asp Val Gly Ser Asn Lys Gly Ala
31
Ile Ile Gly Leu Met Val Gly Gly Val Val
41
Ile Ala Thr (SEQ ID NO: 1)
or a sequence which is substantially homologous thereto.

"Alkyl" refers to monovalent alkyl groups preferably having from 1 to 10 carbon atoms and more preferably 1 to 6 carbon atoms. This term is exemplified by groups such as methyl, ethyl, n-propyl, iso-propyl, n-butyl, iso-butyl, n-hexyl, and the like.

"Alkylene" refers to divalent alkylene groups preferably having from 1 to 10 carbon atoms and more preferably 1to 6 carbon atoms. This term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like.

"Alkaryl" refers to -alkylene-aryl groups preferably having from 1 to 10 carbon atoms in the alkylene moiety and from 6 to 10 carbon atoms in the aryl moiety. Such alkaryl groups are exemplified by benzyl, phenethyl and the like.

"Alkoxy" refers to the group "alkyl-O—" where alkyl is as defined herein. Preferred alkoxy groups include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Alkoxycarbonyl" refers to the group "alkyl-O—C(O)—" wherein alkyl is as defined herein. Such groups include, by way of example, methoxycarbonyl, ethoxycarbonyl, n-propoxycarbonyl, iso-propoxycarbonyl, n-butoxycarbonyl, tert-butoxycarbonyl, sec-butoxycarbonyl, n-pentoxycarbonyl, n-hexoxycarbonyl, and the like.

"Alkylalkoxy" refers to the group "-alkylene-O-alkyl" wherein alkylene and alkoxy are as defined herein. Such groups include, by way of example, methylmethoxy (—$CH_2OCH_3$), ethylmethoxy (—$CH_2CH_2OCH_3$), n-propyl-iso-propoxy (—$CH_2CH_2CH_2OCH(CH_3)_2$), methyl-tert-butoxy (—$CH_2$—O—$C(CH_3)_3$) and the like.

"Alkylthioalkoxy" refers to the group "-alkylene-S-alkyl" wherein alkylene and alkoxy are as defined herein. Such groups include, by way of example, methylthiomethoxy (—$CH_2SCH_3$), ethylthiomethoxy (—$CH_2CH_2SCH_3$), n-propyl-iso-thiopropoxy (—$CH_2CH_2CH_2SCH(CH_3)_2$), methyl-tert-thiobutoxy (—$CH_2SC(CH_3)_3$) and the like.

"Alkenyl" refers to alkenyl groups preferably having from 2 to 10 carbon atoms and more preferably 2 to 6 carbon atoms and having at least 1 and preferably from 1–2 sites of alkenyl unsaturation. Preferred alkenyl groups include ethenyl (—CH=$CH_2$), n-propenyl (—$CH_2$CH=$CH_2$), iso-propenyl (—$C(CH_3)$=$CH_2$), but-2-enyl (—$CH_2$CH=$CHCH_3$) and the like.

"Alkynyl" refers to alkynyl groups preferably having from 2 to 10 carbon atoms and more preferably 2 to 6 carbon atoms and having at least 1 and preferably from 1–2 sites of alkynyl unsaturation. Preferred alkynyl groups include ethynyl (—C≡CH), propargyl (—$CH_2$C≡CH) and the like.

"Acyl" refers to the groups alkyl-C(O)—, aryl-C(O)—, and heteroaryl-C(O)—where alkyl, aryl and heteroaryl are as defined herein.

"Acylamino" refers to the group —C(O)NRR where each R is independently hydrogen or alkyl where alkyl is as defined herein.

"Alkcycloalkyl" refers to the group -alkylene-cycloalkyl wherein alkylene and cycloalkyl are as defined herein.

"Aminoacyl" refers to the group —NRc(O)R where each R is independently hydrogen or alkyl where alkyl is as defined herein.

"Acyloxy" refers to the groups alkyl-C(O)O—, aryl-C(O)O—, heteroaryl-C(O)O—, and heterocyclic-C(O)O—where alkyl, aryl, heteroaryl and heterocyclic are as defined herein.

"Aminoacyloxy" refers to the groups —NRC(O)O-alkyl, —NRC(O)O-substituted alkyl, —NRC(O)O-cycloalkyl, —NRC(O)O-aryl, —NRC(O)O-heteroaryl-, and —NRC(O)O-heterocyclic where R is hydrogen, alkyl, substituted alkyl, cycloalkyl, aryl, heteroaryl, and heterocyclic and where each of alkyl, substituted alkyl, cycloalkyl, aryl, heteroaryl and heterocyclic are as defined herein.

"Oxyacylamino" refers to the groups —OC(O)NR-alkyl, —OC(O)NR-substituted alkyl, —OC(O)NR-aryl, —OC(O)NR-heteroaryl-, and —OC(O)NR-heterocyclic where R is hydrogen, alkyl, substituted alkyl, cycloalkyl, aryl, heteroaryl, and heterocyclic and where each of alkyl, substituted alkyl, cycloalkyl, aryl, heteroaryl and heterocyclic are as defined herein.

"Aryl" refers to an unsaturated aromatic carbocyclic group of from 6 to 14 carbon atoms having a single ring (e.g., phenyl) or multiple condensed rings (e.g., naphthyl or anthryl). Preferred aryls include phenyl, naphthyl and the like.

Unless otherwise constrained by the definition for the aryl substituent, such aryl groups can optionally be substituted with from 1 to 3 substituents selected from the group consisting of hydroxy, acyl, acyloxy, alkyl, alkoxy, alkenyl, alkynyl, amino, aminoacyl, aryl, aryloxy, carboxyl, alkoxycarbonyl, acylamino, cyano, halo, nitro, heteroaryl, trihalomethyl and the like. Preferred substituents include alkyl, alkoxy, halo, cyano, nitro, trihalomethyl, and thioalkoxy.

"Aryloxy" refers to the group aryl-O— wherein the aryl group is as defined above including optionally substituted aryl groups as also defined above.

"Caboxylalkyl" refers to the group —C(O)(O)-alkyl where alkyl is as defined herein.

"Cycloalkyl" refers to cyclic alkyl groups of from 3 to 10 carbon atoms having a single cyclic ring or multiple condensed rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantanyl, and the like.

"Cycloalkenyl" refers to cyclic alkenyl groups of from 4 to 8 carbon atoms having a single cyclic ring and at least one point of internal unsaturation which can be optionally substituted with from 1 to 3 alkyl groups. Examples of suitable cycloalkenyl groups include, for instance, cyclobut-2-enyl, cyclopent-3-enyl, cyclooct-3-enyl and the like.

"Halo" or "halogen" refers to fluoro, chloro, bromo and iodo and preferably is either chloro or fluoro.

"Heteroaryl" refers to a monovalent aromatic group of from 2 to 8 carbon atoms and 1 to 4 heteroatoms selected from oxygen, nitrogen and sulfur within the ring.

Unless otherwise constrained by the definition for the heteroaryl substituent, such heteroaryl groups can be optionally substituted with 1 to 3 substituents selected from the group consisting of alkyl, alkoxy, aryl, aryloxy, halo, nitro, heteroaryl, thioalkoxy, thioaryloxy and the like. Such heteroaryl groups can have a single ring (e.g., pyridyl or furyl)

or multiple condensed rings (e.g., indolizinyl or benzothienyl). Preferred heteroaryls include pyridyl, pyrrolyl and furyl.

"Heterocycle" or "heterocyclic" refers to a monovalent saturated or unsaturated group having a single ring or multiple condensed rings, from 1 to 8 carbon atoms and from 1 to 4 hetero atoms selected from nitrogen, sulfur or oxygen within the ring.

Unless otherwise constrained by the definition for the heterocyclic substituent, such heterocyclic groups can be optionally substituted with 1 to 3 substituents selected from the group consisting of alkyl, alkoxy, aryl, aryloxy, halo, nitro, heteroaryl, thioalkoxy, thioaryloxy and the like. Such heterocyclic groups can have a single ring (e.g., piperidinyl or tetrahydrofuryl) or multiple condensed rings (e.g., indolinyl, dihydrobenzofuran or quinuclidinyl). Preferred heterocycles include piperidinyl, pyrrolidinyl and tetrahydrofuryl.

Examples of heterocycles and heteroaryls include, but are not limited to, furan, thiophene, thiazole, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, pyrrolidine, indoline and the like.

"Thiol" refers to the group —SH.

"Thioalkoxy" refers to the group —S-alkyl.

"Thioaryloxy" refers to the group aryl-S— wherein the aryl group is as defined above including optionally substituted aryl groups as also defined above.

"Thioheteroaryloxy" refers to the group heteroaryl-S— wherein the heteroaryl group is as defined above including optionally substituted aryl groups as also defined above.

The class of biological reagent having the described properties are defined by formula I below:

A—B—C    I wherein
A is selected from the group consisting of compounds defined by formulas II, III, IV and V as described below;
B is selected from the group consisting of
  a) $(CH_2CH(R)Q)_n$
  b) alkylene-Q
  c) substituted alkylene-Q
    wherein R is selected from hydrogen, alkyl, aryl and Q is selected from —O—, —S—, —NH—, —OC(O)NH—, —NHC(O)O—, —NHC(O)NH—, —NHC(O)— and —C(O)NH— and
C is selected from the group consisting of a solid support and a detectable marker optionally linked to Q through a linking arm.

In one embodiment, A comprises a group defined by Formula II below::

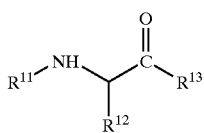

II wherein $R^{11}$ is selected from the group consisting of:

(a) a substituted phenyl group of the formula:

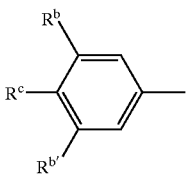

wherein
$R^c$ is selected from the group consisting of acyl, alkyl, alkoxy, alkoxycarbonyl, alkylalkoxy, azido, cyano, halo, hydrogen, nitro, trihalomethyl, thioalkoxy, and wherein $R^b$ and $R^c$ are fused to form a heteroaryl or heterocyclic ring with the phenyl ring wherein the heteroaryl or heterocyclic ring contains from 3 to 8 atoms of which from 1 to 3 are heteroatoms independently selected from the group consisting of oxygen, nitrogen and sulfur;
$R^b$ and $R^{b'}$ are independently selected from the group consisting of hydrogen, halo, nitro, cyano, trihalomethyl, alkoxy, and thioalkoxy with the proviso that $R^b$, $R^{b'}$ and $R^c$ are not all hydrogen and with the further proviso that when $R^c$ is hydrogen, then neither $R^b$ nor $R^{b'}$ are hydrogen;
(b) 2-naphthyl; and
(c) 2-naphthyl substituted at the 4, 5, 6, 7 and/or 8 positions with 1 to 5 substituents selected from the group consisting of alkyl, alkoxy, halo, cyano, nitro, trihalomethyl, and thioalkoxy;

$R^{12}$ is selected from the group consisting of hydrogen, alkyl of from 1 to 4 carbon atoms, alkylalkoxy of from 1 to 4 carbon atoms and alkylthioalkoxy of from 1 to 4 carbon atoms; and $R^{13}$ is selected from the group consisting of —O—, —S—, —O—$(CH_2)_pC(O)$—, —O—$(CH_2)_pC(O)O$— and —O—$(CH_2)_pC(O)NH$—, wherein p is an integer of from 1 to 2.

In formula II above, $R^{11}$ substituted phenyls are preferably 4-substituted, 3,5-disubstituted or 3,4-disubstituted phenyl substituents wherein the substituents at the 3 and/or 5 positions are defined by $R^b$, $R^{b'}$ as above and the substituent at the 4 position is defined by $R^c$ as above. Particularly preferred 3,5-disubstituted phenyls include, by way of example, 3,5-dichlorophenyl, 3,5-difluorophenyl, 3,5-di(trifluoromethyl)phenyl, 3,5-dimethoxyphenyl, and the like. Particularly, preferred 3,4-disubstituted phenyls include, by way of example, 3,4-dichlorophenyl, 3,4-difluorophenyl, 3-(trifluoromethyl)-4-chlorophenyl, 3-chloro-4-cyanophenyl, 3-chloro-4-iodophenyl, 3,4-methylenedioxyphenyl, 3,4-ethylenedioxyphenyl, and the like. Particularly preferred 4-substituted phenyls include, by way of example, 4-azidophenyl, 4-bromophenyl, 4-chlorophenyl, 4-cyanophenyl, 4-ethylphenyl, 4-fluorophenyl, 4-iodophenyl, 4-(phenylcarbonyl)phenyl, 4-(1-ethoxy)ethylphenyl, 4-(ethoxycarbonyl)phenyl, and the like.

In the compounds of formula II, $R^b$ and $R^c$ can be fused to form a heteroaryl or heterocyclic ring with the phenyl ring. Fusion in this manner results in a fused bicyclic ring structure of the formula:

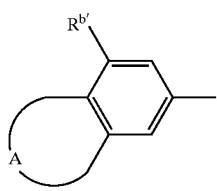

where $R^{b'}$ is as defined above and A is the fused heteroaryl or heterocyclic group containing from 3 to 8 atoms of which from 1 to 3 are heteroatoms independently selected from the group consisting of oxygen, nitrogen and sulfur wherein the two atoms of the phenyl ring are included in the total atoms present in the heteroaryl or heterocyclic group. Examples of such fused ring systems include, for instance, indol-5-yl, indol-6-yl, thionaphthen-5-yl, thionaphthen-6-yl, isothionaphthen-5-yl, isothionaphthen-6-yl, indoxazin-5-yl, indoxazin-6-yl, benzoxazol-5-yl, benzoxazol-6-yl, anthranil-5-yl, anthranil-6-yl, quinolin-6-yl, quinolin-7-yl, isoquinolin-6-yl, isoquinolin-7-yl, cinnolin-6-yl, cinnolin-7-yl, quinazolin-6-yl, quinazolin-7-yl, benzofuran-5-yl, benzofuran-6-yl, isobenzofuran-5-yl, isobenzofuran-6-yl, and the like.

Other preferred $R^{11}$ substituents include, by way of example, 2-naphthyl, 2-methylquinolin-6-yl, benzothiazol-6-yl, 5-indolyl, and the like.

Preferably $R^{12}$ is selected from the group consisting of alkyl of from 1 to 4 carbon atoms, alkylalkoxy of from 1 to 4 carbon atoms and alkylthioalkoxy of from 1 to 4 carbon atoms. Particularly preferred $R^{12}$ substituents include, by way of example, methyl, ethyl, n-propyl, iso-butyl, and the like.

Preferred $R^{13}$ substituents include methoxy, ethoxy, iso-propoxy, n-propoxy, n-butoxy, iso-butoxy, cyclopentoxy, allyloxy, 4-methylpentoxy, —O—CH$_2$-(2,2-dimethyl-1,3-dioxolan-4-yl), —O—CH$_2$-cyclohexyl, —O—CH$_2$-(3-tetrahydrofuranyl), —O—CH$_2$—C(O)O-tert-butyl, —O—CH$_2$—C(CH$_3$)$_3$, —O—CH$_2$-ϕ, —OCH$_2$CH(CH$_2$CH$_3$)$_2$, —O(CH$_2$)$_3$CH(CH$_3$)$_2$, —ON═C(NH$_2$)ϕ, —ON═C(NH$_2$)CH$_3$, —ON═C(NH$_2$)CH$_2$CH$_3$, —ON═C(NH$_2$)CH$_2$CH$_2$CH$_3$, —ON═C(NH$_2$)-cyclopropyl, —ON═C(NH$_2$)—CH$_2$-cyclopropyl, —ON═C(NH$_2$)-cyclopentyl, —ON═C(NH$_2$)CH$_2$CH(CH$_3$)$_2$, and the like.

In another embodiment, A comprises the compounds of Formula III set forth below:

III

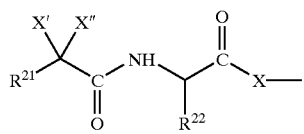

wherein $R^{21}$ is selected from the group consisting of
a) alkyl, alkenyl, alkcycloalkyl, phenyl-$(R^d)_m$—, naphthyl-$(R^d)_m$— wherein $R^d$ is an alkylene group of from 1 to 8 carbon atoms and m is an integer equal to 0 or 1, cycloalkyl, cycloalkenyl, 3-pyridyl, 4-pyridyl and heteroaryl, other than 3- and 4-pyridyl, of 3 to 10 atoms and 1 to 4 heteroatoms selected from oxygen, sulfur and nitrogen wherein the heteroaryl group is optionally substituted with 1 to 3 substituents selected from the group consisting of alkyl, alkoxy, aryl, aryloxy, halo, nitro, thioalkoxy, and thioaryloxy with the proviso that for such heteroaryls when there is at least one nitrogen heteroatom, there is also at least one oxygen and/or sulfur heteroatom;

(b) a substituted phenyl group of the formula:

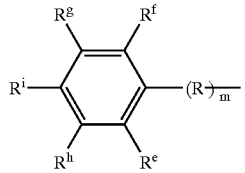

wherein
R is alkylene of from 1 to 8 carbon atoms,
m is an integer equal to 0 or 1,
$R^e$ and $R^f$ are independently selected from the group consisting of hydrogen, hydroxy, fluoro and methyl;
$R^g$ and $R^h$ are independently selected from the group consisting of hydrogen, alkyl, alkoxy, aryl, cyano, cycloalkyl, halo, heteroaryl, heterocyclic, nitro, trihalomethyl, thioalkoxy, thioaryloxy, thioheteroaryloxy, and —C(O)$R^j$ where $R^j$ is selected from the group consisting of alkyl, aryl, alkoxy and aryloxy; and
$R^i$ is selected from the group consisting of hydrogen, alkyl, aryl, cyano, halo, nitro, and where $R^g$ and $R^i$ are fused to form a methylenedioxy ring with the phenyl ring; and
when $R^g$ and/or $R^h$ and/or $R^i$ is fluoro, chloro, bromo and/or nitro, then $R^e$ and/or $R^f$ can also be chloro; and (c) 1- or 2-naphthyl-$(R^k)_m$-substituted at the 5, 6, 7 and/or 8 positions with 1 to 4 substituents selected from the group consisting alkyl, alkoxy, halo, cyano, nitro, trihalomethyl, and thioalkoxy wherein $R^k$ is an alkylene group of from 1 to 8 carbon atoms and m is an integer equal to 0 or 1;

$R^{22}$ is selected from the group consisting of hydrogen, alkyl, phenyl, alkylalkoxy, alkylthioalkoxy;

X is oxygen or sulfur;

X' is hydrogen, hydroxy or fluoro; and

X" is hydrogen, hydroxy or fluoro, or X' and X" together form an oxo group.

In formula III above, preferred $R^{21}$ unsubstituted aryl groups include, for example, phenyl, 1-naphthyl, 2-naphthyl, and the like.

Preferred $R^{21}$ substituted aryl groups include, for example, monosubstituted phenyls having a single substitution at the 2, 3 or 4 positions where each of the particular subsituents is governed by the respective $R^e/R^f$, $R^g/R^h$ and $R^i$ groups; disubstituted phenyls which include those having two substituents at the 2,3-positions, 2,4-positions, 2,5-positions, 2,6-positions, 3,4-positions, 3,5-positions or 3,6-positions where each of these substituents is governed by the respective $R^e$, $R^f$, $R^g$, $R^h$ and $R^i$ groups; and trisubstituted phenyls which include those having three substituents at the 2,3,4-positions, 2,3,5-positions, 2,3,6-positions, 3,4,5-positions and 3,4,6-positions again where each of these substituents is governed by the respective $R^e$, $R^f$, $R^g$, $R^h$ and $R^i$ groups. Preferably, the substituted phenyl groups do not include more than 3 substituents.

Examples of substituted phenyls include, for instance, 4-fluorophenyl, 4-chlorophenyl, 4-bromophenyl, 4-nitrophenyl, 4-methylphenyl, 3-methoxy-phenyl, 3-nitrophenyl, 3-fluorophenyl, 3-chlorophenyl, 3-bromophenyl, 3-thiomethoxyphenyl, 3-methylphenyl, 3-trifluoromethylphenyl, 2-hydroxy-phenyl, 2-methylphenyl, 2-fluorophenyl, 3,4-dichlorophenyl, 3,4- methylene-dioxyphenyl, 3,5-difluorophenyl, 3,5-dichlorophenyl, 2,4-dichlorophenyl, and 2,5-difluorophenyl.

Preferred $R^{21}$ groups represented by phenyl-R— include, by way of example, benzyl, 3-phenylethyl, 4-phenyl-n-propyl, and the like.

Preferred $R^{21}$ alkyl, alkcycloalkyl, cycloalkyl and cycloalkenyl groups include, by way of example, sec-butyl, cyclopropyl, cyclobutyl, cyclohexyl, cyclopentyl, cyclohex-1-enyl, —CH$_2$-cyclopropyl, —CH$_2$-cyclobutyl, —CH$_2$-cyclohexyl, —CH$_2$-cyclopentyl, —CH$_2$CH$_2$-cyclopropyl, —CH$_2$CH$_2$-cyclobutyl, —CH$_2$CH$_2$-cyclohexyl, —CH$_2$CH$_2$-cyclopentyl, and the like.

Preferred $R^{21}$ heteroaryls and substituted heteroaryls include, by way of example, pyrid-3-yl, pyrid-4-yl, thien-2-yl, thien-3-yl, benzothiazol-4-yl, 2-phenylbenzoxazol-5-yl, furan-2-yl, benzofuran-2-yl, benzothiophen-3-yl, 2-chlorothien-5-yl, 3-methylisoxazol-5-yl, 2-(phenylthio)thien-5-yl, 6-methoxythiophen-2-yl, 3-phenyl-1,2,4-thiooxadiazol-5-yl, 2-phenyloxazol-4-yl, and the like.

Preferably $R^{22}$ is selected from the group consisting of alkyl of from 1 to 4 carbon atoms, phenyl, alkylalkoxy of from 1 to 4 carbon atoms and alkylthioalkoxy of from 1 to 4 carbon atoms. Particularly preferred $R^{22}$ substituents include, by way of example, methyl, ethyl, n-propyl, iso-propyl, n-butyl, iso-butyl, —CH$_2$CH$_2$SCH$_3$, cyclohexyl and phenyl.

When X is oxygen, preferred $R^{23}$ substituents include, for example, methyl, ethyl, iso-propyl, n-propyl, n-butyl, iso-butyl, cyclopentyl, allyl, iso-but-2-enyl, 3-methylpentyl, —CH$_2$-cyclopropyl, —CH$_2$-cyclohexyl, —CH$_2$-(3-tetrahydrofuranyl), —CH$_2$-thien-2-yl, —CH$_2$(1-methyl)cyclopropyl, —CH$_2$-thien-3-yl, —CH$_2$—C(O)O-t-butyl, —CH$_2$—C(CH$_3$)$_3$, —CH$_2$CH(CH$_2$CH$_3$)$_2$, -2-methylcyclopentyl, -cyclohex-2-enyl, —CH[CH(CH$_3$)$_2$]COOCH$_3$, —CH$_2$CH$_2$N(CH$_3$)$_2$, —CH$_2$C(CH$_3$)=CH$_2$, —CH$_2$CH=C(CH$_3$)$_2$ and the like.

When X is sulfur, preferred $R^{23}$ substituents include, for example, iso-but-2-enyl and iso-butyl.

In another embodiment, A comprises the compounds set forth in Formula IV below:

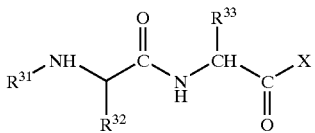

IV wherein $R^{31}$ is selected from the group consisting of
(a) phenyl,
(b) a substituted phenyl group of the formula:

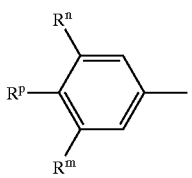

wherein
$R^p$ is selected from the group consisting of acyl, alkyl, alkoxy, alkylalkoxy, azido, cyano, halo, hydrogen, nitro, trihalomethyl, thioalkoxy, and wherein $R^p$ and $R^m$ are fused to form a heteroaryl or heterocyclic ring with the phenyl ring,
$R^m$ and $R^n$ are independently selected from the group consisting of hydrogen, halo, nitro, cyano, trihalomethyl, alkoxy, and thioalkoxy with the proviso that when $R^p$ is hydrogen, then $R^m$ and $R^n$ are either both hydrogen or both substituents other than hydrogen,
(c) 2-naphthyl,
(d) 2-naphthyl substituted at the 4, 5, 6, 7 and/or 8 positions with 1 to 5 substituents selected from the group consisting of alkyl, alkoxy, halo, cyano, nitro, trihalomethyl, thioalkoxy, aryl, and heteroaryl,
(e) heteroaryl, and
(f) substituted heteroaryl containing 1 to 3 substituents selected from the group consisting of alkyl, alkoxy, aryl, aryloxy, cyano, halo, nitro, heteroaryl, thioalkoxy and thioaryloxy provided that said substituents are not ortho (adjacent) to the heteroaryl attachment to the —NH group;

$R^{32}$ is selected from the group consisting of hydrogen, alkyl of from 1 to 4 carbon atoms, alkylalkoxy of from 1 to 4 carbon atoms, alkylthioalkoxy of from 1 to 4 carbon atoms, aryl, heteroaryl, substituted aryl and substituted heteroaryl provided that the substituents are not ortho (adjacent) to the attachment of the aryl or heteroaryl atom to the carbon atom;

$R^{33}$ is selected from the group consisting of alkyl, alkenyl, alkynyl, aryl, cycloalkyl, cycloalkenyl, heteroaryl, substituted alkyl, substituted alkenyl, substituted alkynyl, and heterocyclic; and X is selected from the group consisting of oxygen and sulfur.

In formula IV above, $R^{31}$ substituted phenyls are preferably 4-substituted, 3,5-disubstituted or 3,4-disubstituted phenyl substituents wherein the substituents at the 3 and/or 5 positions are defined by $R^m$, $R^{m'}$ as above and the substituents at the 4 position is defined by $R^l$ as above. Particularly preferred 3,5-disubstituted phenyls include, by way of example, 3,5-dichlorophenyl, 3,5-difluorophenyl, 3,5-di(trifluoromethyl)phenyl, 3,5-dimethoxyphenyl, and the like. Particularly, preferred 3,4-disubstituted phenyls include, by way of example, 3,4-dichlorophenyl, 3,4-difluorophenyl, 3-(trifluoromethyl)-4-chlorophenyl, 3-chloro-4-cyanophenyl, 3-chloro-4-iodophenyl, 3,4-methylenedioxyphenyl, and the like. Particularly preferred 4-substituted phenyls include, by way of example, 4-azidophenyl, 4-bromophenyl, 4-chlorophenyl, 4-cyanophenyl, 4-ethylphenyl, 4-fluorophenyl, 4-iodophenyl, 4-(phenylcarbonyl)phenyl, 4-(1-ethoxy)ethylphenyl, and the like.

Other preferred $R^{31}$ substituents include, by way of example, 2-naphthyl, quinolin-3-yl, 2-methylquinolin-6-yl, benzothiazol-6-yl, benzothiazol-2-yl, 5-indolyl, phenyl, 2-naphthyl, and the like.

In the compounds of formula IV, $R^p$ and $R^m$ can be fused to form a heteroaryl or hetero cyclic ring with the phenyl ring. Fusion in this manner results in a fused bicyclic ring structure of the formula:

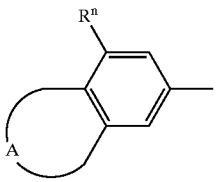

where $R^n$ is as defined above and A is the fused heteroaryl or heterocyclic group as these terms are as defined above wherein the two atoms of the phenyl ring are included in the total atoms present in the heteroaryl or heterocyclic group. Examples of such fused ring systems include, for instance, indol-5-yl, indol-6-yl, thionaphthen-5-yl, thionaphthen-6-yl, isothionaphthen-5-yl, isothionaphthen-6-yl, indoxazin-5-yl, indoxazin-6-yl, benzoxazol-5-yl, benzoxazol-6-yl, anthranil-5-yl, anthranil-6-yl, quinolin-6-yl, quinolin-7-yl, isoquinolin-6-yl, isoquinolin-7-yl, cinnolin-6-yl, cinnolin-7-yl, quinazolin-6-yl, quinazolin-7-yl, benzofuran-5-yl, benzofuran-6yl, isobenzofuran-5-yl, isobenzofuran-6-yl, and the like.

Preferably $R^{32}$ is selected from the group consisting of alkyl of from 1 to 4 carbon atoms, alkylalkoxy of from 1 to 4 carbon atoms, alkylthioalkoxy of from 1 to 4 carbon atoms, aryl, heteroaryl, substituted aryl and substituted heteroaryl provided that the substituents are not ortho to the attachment of the aryl or heteroaryl atom to the carbon atom. Particularly preferred $R^{32}$ substituents include, by way of example, methyl, ethyl, n-propyl, iso-propyl, n-butyl, iso-butyl, —$CH_2CH_2SCH_3$, phenyl and the like.

Preferred $R^{33}$ substituents include alkyl groups such as methyl, ethyl, n-propyl, iso-propyl, n-butyl, iso-butyl, sec-butyl, and the like; substituted alkyl groups such as a-hydroxyethyl, —$CH_2$-cyclohexyl, benzyl, p-hydroxybenzyl, 3-iodo-4-hydroxybenzyl, 3,5-diiodo-4-hydroxybenzyl, —$CH_2$-indol-3-yl, phenyl, —$(CH_2)_4$—NH—BOC, —$(CH_2)_4$—$NH_2$, —$CH_2$-(1-N-benzyl-imidazol-4-yl), —$CH_2$-imidazol-4-yl, —$CH_2CH_2SCH_3$, —$(CH_2)_4NHC(O)(CH_2)_4CH_3$, —$(CH_2)_yC(O)OR^{35}$ where y is 1 or 2 and $R^{35}$ is hydrogen, methyl, tert-butyl, phenyl, and the like.

In another embodiment, A comprises the compounds represented by Formula V set forth below:

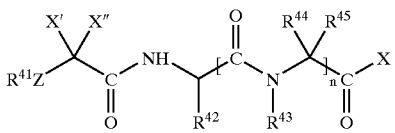

V wherein
$R^{41}$ is selected from the group consisting of alkyl, alkenyl, alkynyl, cycloalkyl, cycloalkenyl, substituted alkyl, substituted alkenyl, substituted alkynyl, aryl, heteroaryl and heterocyclic;
$R^{42}$ is selected from the group consisting of hydrogen, alkyl, substituted alkyl, alkenyl, substituted alkenyl, alkynyl, substituted alkynyl, cycloalkyl, aryl, heteroaryl and heterocyclic;
each $R^{43}$ is independently selected from the group consisting of hydrogen and methyl and $R^{43}$ together with $R^{44}$ can be fused to form a cyclic structure of from 3 to 8 atoms which is optionally fused with an aryl or heteroaryl group;
each $R^{44}$ is independently selected from the group consisting of hydrogen, alkyl, alkenyl, alkynyl, aryl, cycloalkyl, cycloalkenyl, heteroaryl, heterocyclic, substituted alkyl, substituted alkenyl and substituted alkynyl;
each $R^{45}$ is selected from hydrogen and methyl or together with $R^{43}$ forms a cycloalkyl group of from 3 to 6 carbon atoms;
X is selected from oxygen, sulfur and NH;
X' is hydrogen, hydroxy or fluoro; and
X" is hydrogen, hydroxy or fluoro, or X' and X" together form an oxo group;

Z is selected from the group consisting of a bond covalently linking $R^{41}$ to —CX'X"—, oxygen and sulfur; and
n is an integer equal to 1 to 3.

In formula V above, X" is preferably hydrogen and X' is preferably hydrogen or fluoro.

In formula V above, Z is preferably a covalent bond linking $R^1$ to —CX'X"—.

In formula V above, preferred $R^{41}$ unsubstituted aryl groups include, for example, phenyl, 1-naphthyl, 2-naphthyl, and the like.

Preferred $R^{41}$ substituted aryl groups include, for example, monosubstituted phenyls (preferably 3 or 5 substituents); disubstituted phenyls (preferably 3,5 substituents); and trisubstituted phenyls (preferably 3,4,5 substituents). Preferably, the substituted phenyl groups do not include more than 3 substituents.

Examples of substituted phenyls include, for instance, 4-fluorophenyl, 4-chlorophenyl, 4-bromophenyl, 4-nitrophenyl, 4-methylphenyl, 3-methoxy-phenyl, 3-nitrophenyl, 3-fluorophenyl, 3-chlorophenyl, 3-bromophenyl, 3-thiomethoxyphenyl, 3-methylphenyl, 3-trifluoromethylphenyl, 2-hydroxy-phenyl, 2-methylphenyl, 2-fluorophenyl, 2-chlorophenyl, 3,4-difluorophenyl, 2,3,4,5,6-pentafluorophenyl, 3,4-dibromophenyl, 3,4-dichlorophenyl, 3,4-methylene-dioxyphenyl, 3,5-difluorophenyl, 3,5-dichlorophenyl, 2,4-dichlorophenyl, and 2,5-difluorophenyl.

Preferred $R^{41}$ alkaryl groups include, by way of example, benzyl, 2-phenylethyl, 3-phenyl-n-propyl, and the like.

Preferred $R^{41}$ alkyl, substituted alkyl, alkenyl, cycloalkyl and cycloalkenyl groups include, by way of example, iso-propyl, n-propyl, n-butyl, iso-butyl, sec-butyl, tert-butyl, —$CH_2CH=CH_2$, —$CH_2CH=CH(CH_2)_4CH_3$, cyclopropyl, cyclobutyl, cyclohexyl, cyclopentyl, cyclohex-1-enyl, —$CH_2$-cyclopropyl, —$CH_2$-cyclobutyl, —$CH_2$-cyclohexyl, —$CH_2$-cyclopentyl, —$CH_2CH_2$-cyclopropyl, —$CH_2CH_2$-cyclobutyl, —$CH_2CH_2$-cyclohexyl, —$CH_2CH_2$-cyclopentyl, aminomethyl, N-tert-butoxycarbonylaminomethyl, and the like.

Preferred $R^{41}$ heteroaryls and substituted heteroaryls include, by way of example, pyrid-2-yl, pyrid-3-yl, pyrid-4-yl, fluoropyridyls (including 5-fluoropyrid-3-yl), chloropyridyls (including 5-chloropyrid-3-yl), thien-2-yl, thien-3-yl, benzothiazol-4-yl, 2-phenylbenzoxazol-5-yl, furan-2-yl, benzofuran-2-yl, thionaphthen-2-yl, 2-chlorothiophen-5-yl, 3-methylisoxazol-5-yl, 2-(thiophenyl)thiophen-5-yl, 6-methoxythionaphthen-2-yl, 3-phenyl-1,2,4-thiooxadiazol-5-yl, 2-phenyloxazol-4-yl, and the like.

Preferably $R^{42}$ is selected from the group consisting of hydrogen, alkyl, substituted alkyl, cycloalkyl, aryl, heteroaryl and heterocyclic. Particularly preferred $R^{42}$ substituents include, by way of example, methyl, ethyl, n-propyl, iso-propyl, n-butyl, iso-butyl, sec-butyl, phenyl, 4-fluorophenyl, 3,5-difluoro-phenyl, 4-methoxyphenyl, benzyl, cyclopropyl, cyclohexyl, cyclopentyl, cycloheptyl, thien-2-yl, thien-3-yl, —$CH_2CH_2SCH_3$, —$CH_2OCH_2\phi$, —$CH(CH_3)OCH_2\phi$, —$CH(OH)CH_3$, —$CH_2OH$ and the like. As noted below, $R^{42}$ (as well as $R^{44}$) is preferably the side chain of an L-amino acid.

Preferably, $R^{43}$ is hydrogen, methyl or together with R44 and the nitrogen to which $R^{43}$ is attached forms pyrrolidin-2-yl, 2,3-dihydroindol-2-yl, piperidin-2-yl, 4-hydroxy-pyrrolidin-2-yl, 1,2,3,4-tetrahydroisoquinolin-3-yl, and the like.

Preferred $R^{44}$ substituents include, for example, hydrogen, methyl, ethyl, iso-propyl, n-propyl, n-butyl, sec-butyl, iso-butyl, cyclopentyl, cyclohexyl, allyl, iso-but-2-enyl, 3-methylpentyl, —$CH_2$-cyclopropyl, —$CH_2$-cyclohexyl, —$CH_2$-indol-3-yl, phenyl, p-(phenyl)phenyl, m-(phenyl)phenyl o-fluorophenyl, m-fluorophenyl, p-fluorophenyl, p-bromophenyl, m-methoxyphenyl, p-methoxyphenyl, phenethyl, benzyl, m-hydroxybenzyl, p-hydroxybenzyl, p-nitrobenzyl, m-trifluoromethylphenyl, p-$(CH_3)_2NCH_2CH_2CH_2O$-benzyl, p-$(CH_3)_3COC(O)CH_2O$-benzyl, p-phenylphenyl, 3,5-difluorophenyl, p-$(HOOCCH_2O)$-benzyl, 2-aminopyrid-6-yl, 4—(N-morpholino-$CH_2CH_2O$)-benzyl, —$CH_2CH_2C(O)NH_2$, —$CH_2$-imidazol-4-yl, —$CH_2$-(3-tetrahydrofuranyl), —$CH_2$-thien-2-yl, —$CH_2$-thiazol-4-yl, —$CH_2$(1-methyl) cyclopropyl, —$CH_2$-thien-3-yl, thien-3-yl, thien-2-yl, —$CH_2$—$C(O)O$—t-butyl, —$CH_2$—$C(CH_3)_3$, —$CH_2CH$ $(CH_2CH_3)_2$, 2-methylcyclopentyl, -cyclohex-2-enyl, —CH $[CH(CH_3)_2]COOCH_3$, —$(CH_2)_2SCH_3$, —$CH_2CH_2N$ $(CH_3)_2$, —$CH_2C(CH_3)$=$CH_2$, —$CH_2CH$=$CHCH_3$ (cis and trans), —$CH_2OH$, —$CH(OH)CH_3$, —$CH(O$—t-butyl) $CH_3$, —$CH_2OCH_3$, —$(CH_2)_4NH$-Boc, —$(CH_2)_4NH_2$, —$(CH_2)_4N(CH_3)_2$, —$CH_2$-pyridyl (e.g., 2-pyridyl, 3-pyridyl and 4-pyridyl), pyridyl (2-pyridyl, 3-pyridyl and 4-pyridyl), —$CH_2$-naphthyl (e.g., 1-naphthyl and 2-naphthyl), —$CH_2$—(N-morpholino), p—(N-morpholino-$CH_2CH_2O$)—benzyl, benzo[b]thiophen-2-yl, benzo[b] thiophen-3-yl, 5-chlorobenzo[b]thiophen-2-yl, 4,5,6,7-tetrahydrobenzo[b]thiophen-2-yl, benzo[b]thiophen-3-yl, tetrazol-5-yl, 5-chlorobenzo[b]thiophen-3-yl, benzo[b] thiophen-5-yl, 6-methoxynaphth-2-yl, —$CH_2$—N-phthalimidyl, 2-methylthiazol4-yl, and thieno[2,3-b] thiophen-2-yl, 5-bromothien-2-yl, 4-bromothien-2-yl, 5-chlorothien-2-yl, 3-phenoxyphenyl, 2-phenoxyphenyl, 4-ethylphenyl, 2-benzylphenyl, (4-ethylphenyl)phenyl, 4-tert-butylphenyl, 4-n-butylphenyl, o-(4-chlorophenoxy) phenyl, furan-2-yl, 4-phenylacetylenylphenyl and the like.

Preferably, $R^{45}$ is hydrogen. However, in another embodiment, $R^{44}$ and $R^{45}$ are fused to form a cycloalkyl group including, for example, cyclopropyl, cyclobutyl, and the like.

"Detectable marker" means a radioactive label, a fluorescent label, a chemiluminescer, a heavy metal ion, an antibody, an enzyme, biotin, an azido group, an immunobiotin and the like.

Conveniently, a radioactive label may be employed. Radioactive labels include $^{125}I$, $^{32}P$, $^3H$, $^{14}C$ and the like. Any radioactive label may be employed which provides for an adequate signal and has sufficient half-life.

Further, a fluorescent label may be employed. Fluorescent labels include fluorescein, rhodamine and its derivatives, dansyl, umbelliferone, BODIPY®, and the like. Any fluorescent label may be employed with provides for an adequate signal. A chemiluminescer may be employed. Suitable chemiluminescers include luciferin, and 2,3-dihydrophthalazinediones, i.e. luminol.

Other labels include ligands, which can serve as a specific binding pair member to a labeled antibody, fluorescers, chemiluminescers, enzymes, photoaffinity probes, antibodies which can serve as a specific binding pair member for a labeled ligand and the like. A wide variety of labels have been employed in immunoassays which can be readily employed in the present methods. The choice of label will be governed by the effect of the label on the rate of binding of the biological reagent to the target. It will be necessary that the label provide sufficient sensitivity to detect the target.

"Solid support" means any solid support in which a compound can be affixed. Examples of these supports include glass, test tubes, microtiter plates, nylon beads, agarose beads, magnetic beads, glass beads, teflon, polystyrene beads, photodetectable chips and the like.

Preferably, the solid support or the detectable marker contain a reactive functional group which is complementary to and reacts with the compounds of Formula VI to form the compounds of Formula I.

"Linking arms" are well known in the art and include, by way of example only, conventional linking arms such as those comprising ester, amide, carbamate, ether, thio ether, urea, amine groups and the like. The linking arm can be cleavable or non-cleavable.

Cleavable linking arms refer to linking arms wherein at least one of the covalent bonds of the linking arm which attaches the compound t o the solid support can be readily broken by specific chemical reactions thereby providing for compounds free of the solid support or detectable marker. The chemical reactions employed to break the covalent bond of the linking arm are selected so as to be specific for bond breakage thereby preventing unintended reactions occurring elsewhere on the compound. The cleavable linking arm is selected relative to the synthesis of the compounds to b e formed on the solid support so as to prevent premature cleavage of this compound from the solid support as well as not to interfere with any of the procedures employed during compound synthesis on the support. Suitable cleavable linking arms are well known in the art.

"Non-cleavable linking arms" refer to linking arms wherein the covalent bond(s) linking the activated ketone compound to the solid support can only be cleaved under conditions which chemically alters unintended parts of the structure of the compound attached thereto.

Compound Preparation

The compounds of formula I above are readily prepared via several divergent synthetic routes with the particular route selected relative to the ease of compound preparation, the commercial availability of starting materials, and the like.

The starting materials for compounds comprising Formula II are readily prepared by the methods set forth in International Patent Application No. PCT/US97/20356[8], which is incorporated by reference herein in its entirety.

The starting materials for compounds comprising Formula III are readily prepared by the methods set forth in International Patent Application No. PCT/US97/20355[9], which is incorporated by reference herein in its entirety.

The starting materials for compounds comprising Formula IV are readily prepared by the methods set forth in International Patent Application No. PCT/US97/18704[10], which is incorporated by reference herein in its entirety.

The starting materials for compounds comprising Formula V are readily prepared by the methods set forth in International Patent Application No. PCT/US97/20804[11], which is incorporated by reference herein in its entirety.

The manner in which the label is bound to the compound will vary depending upon the nature of the label. For a radioactive label, a wide variety of techniques can be employed which are known in the art.

The manner for attaching the biological reagent to a solid support is well known in the art. One method is by derivatizing the end of the linker having a carboxyl or amino group. Another example of attachment is by attaching a biotin molecule to the biological reagent and then attaching the biological reagent to a solid support bearing avidin molecules.

It is recognized that the biological reagent should be attached to the solid support in an orientation which will allow binding of the biological reagent to the protein or peptide of interest.

Methods

The biological reagents of the present invention are useful in determining the mechanism of β-amyloid peptide release and/or its synthesis, and, accordingly, have utility in future drug discovery.

Without being limited to a theory, it is thought that the β-amyloid peptide is generated by the actions of two enzymes, a β-secretase which cleaves the parent protein at the amino terminus of the β-amyloid peptide and a γ-secretase which cleaves the parent protein at the carboxyl terminus of the β-amyloid peptide. It is thought that the compounds of formula I, II, III and IV act to inhibit the cleavage by the γ-secretase, either directly or indirectly via a protein modulating γ-secretase activity.

The biological reagents are useful in identifying the cellular factor (either peptide, protein etc.) whose activity is inhibited by the compounds of formula I, II, III and IV. Such biological reagents can be used is a variety of ways depending on the reactive group which comprises C in Formula I.

In one embodiment, cells known to produce γ-amyloid peptide are disrupted to produce a cell membrane suspension. Such cellular membrane suspensions are passed over the biological reagents of the present invention, wherein C of formula I comprises a solid support. The cellular factor or factors which interacts with the compounds of formula II, III, IV and V, will bind to the biological reagents of the present invention. The remainder of the cellular biological solution will be washed from the biological reagent comprising the solid support. The cellular factor can then be identified.

In another embodiment, cells known to produce β-amyloid peptide are disrupted to produce a cellular membrane suspension. Such cellular membrane suspensions are mixed with the biological reagents of the present invention, wherein C of formula I comprises a photoaffinity reagent, for example an azido group under conditions whereby the cellular factor or factor which interact with the compounds of formula II, III, IV and V will bind. The mixture is then subjected to light, for example, ultraviolet light which covalently links the biiological reagents of the present invention to the cellular factor. The cellular factor bound to the photoaffinity reagent is then removed/purified from the remainder of the biological solution and the cellular factor identified.

In another embodiment, cells known to produce β-amyloid peptide are mixed with the biological reagent of the present invention wherein C of Formula I comprises a fluorescent dye under conditions wherein the biological reagent of the present invention binds to cells comprising the cellular factor or factors involved in the production of β-amyloid peptide. Such cells are then identified by their fluorescence. Methods of identification include, but are not limited to, cell sorting.

It is contemplated that the cells known to produce β-amyloid peptide may include a library of eukaryotic or prokaryotic cells transformed with genes under the control of an expression vector, such that the genes are expressed in the cells. Cells expressing the cellular factor or factors involved in the production of the β-amyloid peptide may be identified by fluorescence. The isolated cells may then be disrupted and the expressed gene and or cellular factor identified.

The cellular factor may be identified by an number of methods, including, without being limited to, peptide sequencing, binding to known antibodies and the like. The gene coding for the cellular factor may be sequenced. By these methods the cellular factor involved in β-amyloid peptide release and/or its synthesis may be identified.

Utility

The compounds of the invention are useful in determining the mechanism for β-amyloid peptide release and/or its synthesis, and, accordingly, have utility in future drug discovery.

In particular the biological reagents may be used to determine cellular agents, such as peptides or proteins involved with β-amyloid peptide release and/or its synthesis. Such identification involves the binding of the biological reagent to the cellular agent in a solution and the extraction of the biological reagent/cellular agent from the solution and the identification of the cellular agent.

The biological reagents may also be used to identify cells which express the cellular agent, such as peptides or protein involved with βamyloid peptide release and/or its synthesis. Such identification would involve labeling of cells expressing the cellular agent by attachment of detectably labelled biological reagents of the present invention to such cells.

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

| | | |
|---|---|---|
| BOC | = | tert-butoxycarbonyl |
| bd | = | broad doublet |
| bs | = | broad singlet |
| cc | = | cubic centimeter |
| d | = | doublet⁺ |
| dd | = | doublet of doublets |
| DMF | = | dimethylformamide |
| DMSO | = | dimethyl sulfoxide |
| EDC | = | 1-(3-dimethylaminopropyl)-ethylcarbodiimide hydrochloride |
| EDTA | = | ethylene diamine tetraacetic acid |
| eq. | = | equivalents |
| ether | = | diethyl ether |
| g | = | grams |
| hept. | = | heptuplet |
| m | = | multiplet |
| M | = | molar |
| max | = | maximum |
| mg | = | milligram |
| min. | = | minutes |
| mL | = | milliliter |
| mM | = | millimolar |
| mmol | = | millimole |
| N | = | normal |
| ng | = | nanogram |
| nm | = | nanometers |
| OD | = | optical density |
| pg | = | picogram |
| pM | = | picomolar |
| φ | = | phenyl |
| psi | = | pounds per square inch |
| q | = | quartet |
| quint. | = | quintuplet |
| rpm | = | rotations per minute |
| s | = | singlet |
| sept | = | septuplet |
| t | = | triplet |
| THF | = | tetrahydrofuran |
| TLC | = | thin layer chromatography |
| μL | = | microliter |
| UV | = | ultraviolet |
| w/v | = | weight to volume |

Additionally, the term "Aldrich" indicates that the compound or reagent used in the following procedures is commercially available from Aldrich Chemical Company, Inc., 1001 West Saint Paul Avenue, Milwaukee, Wis. 53233 USA; the term "Fluka" indicates the compound or reagent is commercially available from Fluka Chemical Corp., 980 South 2nd Street, Ronkonkoma, N.Y. 11779 USA; the term "Lancaster" indicates the compound or reagent is commercially available from Lancaster Synthesis, Inc., P.O. Box 100, Windham, N.H. 03087 USA; and the term "Sigma" indicates the compound or reagent is commercially available from Sigma, P.O. Box 14508, St. Louis, Mo. 63178 USA; the term "Bachem" indicates that the compound or reagent is commercially available from Bachem Biosciences Inc., 3700 Horizon Drive, Renaissance at Gulph Mills, King of Prussia, Pa. 19406 USA; the term "Engelhard" indicates the compound or reagent is commercially available from Engelhard Catalysts & Chemicals Division, 554 Mormon Church Road, Seneca, S.C. 29678; the term "TCI-US" indicates that the compound or reagent is commercially available from TCI America, 9211 North Harborgate Street, Portland Oreg. 97203; the term "Advanced Chemtech" indicates that the compound or reagent is commercially available from Advanced Chemtech, Louisville, Ky.; the term "Molecular Probes" indicates the compound or reagent is commercially available from Molecular Probes, Inc., Eugene, O; and the term "Pierce" indicates the compound or reagent is commercially available from Pierce Chemical Company P.O. 117 Rockford Ill. 61105.

In the examples below, all temperatures are in degrees Celsius (unless otherwise indicated) and the following general procedures were used to prepare the compounds as indicated.

General Procedure A

Boc Protection of Diamine

A solution of the appropriate diamine (8 eq.) dissolved in dioxane (1 M) was treated with a dioxane solution (0.3 M) of di-tert-butyl dicarbonate (1 eq., Aldrich), added over 2.5 hours. The resulting mixture was stirred at room temperature 24 hours then concentrated in vacuo. The crude oil was dissolved in water and extracted with three portions of methylene chloride. The combined organic extracts were washed with water then dried over $Na_2SO_4$, filtered and concentrated to provide the desired mono-Boc protected diamine.

General Procedure B

HOAt Coupling Reaction

A solution of the carboxylic acid component (1 eq.) was dissolved in tetrahydrofuran (THF, 0.1M) and treated sequentially with N-ethyl-N'-(3-dimethylaminopropyl)-carbodiimide hydrochloride (EDC-HCl, 1.1 eq., Bachem) and 1-hydroxy-7-azabenzotriazole (HOAt, 1.1 eq., Aldrich). To the resulting solution was added the amine component (1 eq) after which the mixture was stirred overnight, or until judged complete by TLC analysis. The solvent was then removed in vacuo. The crude oil was diluted with water and extracted twice with methylene chloride. The combined organic extracts were dried over $Na_2SO_4$, filtered and concentrated. Purification of the desired product was accomplished by flash chromatography.

General Procedure C

Cbz Removal by Hydrogenolysis

The Cbz-protected amine was dissolved in methanol (0.4 M) and the resulting solution was purged of oxygen after which an atmosphere of nitrogen was established. The reaction mixture was charged with 5% Pd/C (62 mg/mmol of substrate, Engelhard) then purged with hydrogen. An atmosphere of hydrogen (1 atm., balloon) was maintained overnight. The mixture was then filtered through a pad of celite and the solvent removed in vacuo to afford the crude product. Purification by flash chromatography afforded the desired product.

General Procedure D

Boc Removal

A stream of anhydrous HCl gas was passed through a solution of the Boc-protected amine in 1,4-dioxane at room temperature for 10–15 minutes. A CaSO4 drying tube was placed on the flask and the reaction mixture was stirred overnight. The solvent was removed in vacuo to afford the final product as the HCl-salt.

General Procedure E

EDC Coupling Procedure

A round bottom flask was charged with the corresponding carboxylic acid (1.0 eq.), hydroxybenzotriazole hydrate (1.1 eq.) and the corresponding amine (1.0 eq.) in THF under nitrogen atmosphere. An appropriate amount (1.1 eq for free amines and 2.2 eq. for hydrochloride amine salts) of base, such as Hunig's base was added to the well stirred mixture followed by EDC (1.1 eq.). After stirring from 4 to 17 hours at room temperature the solvent was removed at reduced pressure, the residue taken up in ethyl acetate (or similar solvent) and water, washed with saturated aqueous sodium bicarbonate solution, 1 N HCl, brine, dried over anhydrous sodium sulfate and the solvent removed at reduced pressure to provide the product.

General Procedure F

Ester Hydrolysis to Free Acid

Ester hydrolysis to the free acid was conducted by conventional methods. Below are two examples of such conventional de-esterification methods.

Method A: To a carboxylic ester compound in a 1:1 mixture of $CH_3OH/H_2O$ was added 2–5 equivalents of $K_2CO_3$. The mixture was heated to 50° C. for 0.5 to 1.5 hours until tlc showed complete reaction. The reaction was cooled to room temperature and the methanol was removed on a rotary evaporator. The pH of the remaining aqueous solution was adjusted to ~2, and ethyl acetate was added to extract the product. The organic phase was then washed with saturated aqueous NaCl and dried over $MgSO_4$. The solution was stripped free of solvent on a rotary evaporator to yield the product.

Method B: The amino acid ester was dissolved in dioxane/water (4:1) to which was added LiOH (~2 eq.) that was dissolved in water such that the total solvent after addition was about 2:1 dioxane:water. The reaction mixture was stirred until reaction completion and the dioxane was removed under reduced pressure. The residue was dissolved in water and washed with ether. The layers were separated and the aqueous layer was acidified to pH 2. The aqueous layer was extracted with ethyl acetate. The ethyl acetate extracts were dried over $Na_2SO_4$ and the solvent was removed under reduced pressure after filtration. The residue was purified by conventional methods (e.g., recrystallization).

General Procedure G

BOC Removal Procedure

A stream of anhydrous HCl gas was passed through a stirred solution of the N-t-Boc protected amino acid in 1,4-dioxane (0.03–0.09 M), chilled in a ice bath to ~10° C. under $N_2$, for 10–15 minutes. The solution was capped, the cooling bath removed, and the solution was allowed to warm to room temperature with stirring for 2–8 hours, monitoring by TLC for the consumption of starting material. The solution was concentrated (and in some instances dissolved in $CH_2Cl_2$ then re-concentrated and placed in vacuum oven at 60–70° C. to remove most of the residual dioxane) and used without further purification.

General Procedure H

Synthesis of S-(+)-3,5-Difluoromandelic Acid

Step A.—Preparation of Methyl S-(±)-3,5-difluoromandelate

To a solution of 3,5-difluorobenzaldehyde (Aldrich) in $CH_2Cl_2$ (100 mL) was added $ZnCl_2$ (6.7 g, 21.1 mmol) to form a slurry. Trimethysilyl cyanide (21.0 g, 211.2 mmol) dissolved in $CH_2Cl_2$ (100 mL) was slowly added to the slurry at 0° C. The resulting solution was stirred at room temperature for 4 h. The reaction mixture was then diluted with water and the organic layer separated. The combined organic layers were concentrated to a residue. The residue was dissolved with MeOH (200 mL) at 0° C. and anhydrous HCl gas bubbled into the solution for 10 min. After stirring at room temperature for 18 h, the solution was concentrated to a solid. The solid was dissolved in $CH_2Cl_2/H_2O$ and the aqueous portion extracted with $CH_2Cl_2$. The combined organics were washed with brine, dried over anhydrous $MgSO_4$ and concentrated to a solid (37.4 g, 87.6%), mp=77–78° C.

$^1$H NMR (300 MHz, $CDCl_3$): δ=6.97 (dd, J=9.6 Hz, J=1.79 Hz, 2H), 6.74 (dt, J=8.82, J=2.28 Hz, 1H), 5.14 (d, J=4.64 Hz, 1H), 3.78 (s, 3H), 3.54 (d, J=5.1 Hz, 1H).

Step B—Preparation of Methyl S-(+)-3,5-difluoromandelate

Methyl (±)-3,5-difluoromandelate was separated via preparative chiral HPLC to give a white solid having a melting point of 70–71° C.

$C_9H_8F_2O_3$ (MW=202.17); mass spectroscopy found ($M+NH_4^+$) 220.0.

Anal. calcd for $C_9H_8F_2O_3$: C, 53.47; H, 3.99. Found: C, 53.40; H, 3.89.

Step C—Preparation of S-(+)-3,5-Difluoromandelic acid

A solution of methyl S-(+)-3,5-difluoromandelate (1 eq.) in 74% aqueous THF was cooled to 0° C. and treated with lithium hydroxide. After 40 minutes at 0° C. the reaction was complete by TLC. The contents were transferred to a separatory funnel and partitioned between $CH_2Cl_2$ and saturated aqueous $NaHCO_3$. The aqueous layer was acidified with 0.5 N $NaHSO_4$ and extracted thrice with ethyl acetate. The combined extracts were washed with brine, dried over $Na_2SO_4$, filtered, and concentrated to a white solid having a melting point of 119–122° C. The $^1$H NMR was consistent with known 3,5-difluoromandelic acid.

General Procedure I

Synthesis of BODIPY-containing Compounds

An appropriate amine starting material (2–5 eq.) and Bodipy N-hydroxysuccinimide ester (1 eq., Molecular Probes) was stirred in DMF for 48 hours. The mixture was concentrated to provide a crude solid which was purified by silica gel chromatography.

Example 1

Synthesis of tert-butyl N-(8-amino-3,6-dioxaoctyl) carbamate

Following general procedure A and using 1,8-diamino-3,6-dioxaoctane (Aldrich) the title compound was prepared.

$C_{11}H_{24}N_2O_4$ (MW=248.3); mass spectroscopy (MH$^+$) 249.3.

Anal. Calcd for $C_{11}H_{24}N_2O_4$: C, 53.21; H, 9.74; N, 11.28. Found: C, 52.29; H, 9.07; N, 10.32.

Example 2

Synthesis of Methyl N-2-aminoethyl-N'-2-t-butylcarbamoylethyl amine

Following general procedure A and using N'-methyl-2,2'-diaminodiethylamine (TCI-US) the title compound was prepared.

$C_{10}H_{23}N_3O_2$ (MW=217.3); mass spectroscopy (MH$^+$) 218.2.

Anal. Calcd for $C_{10}H_{23}N_3O_2$: C, 55.27; H, 10.67; N, 19.34. Found: C, 54.54; H, 10.13; N, 18.07.

Example 3

Synthesis of tert-butyl N-(8-N'-(N''-benzyloxycarbonyl-L-phenylglycine)-3,6-dioxaoctyl) carbamate -continued

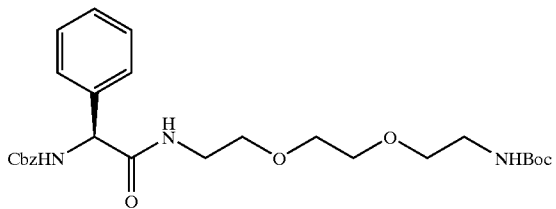

Following general procedure B and using N-Cbz-L-phenylglycine (Bachem) as the carboxylic component and tert-butyl N-(8-amino-3,6-dioxaoctyl) carbamate (from Example 1 above) as the amine component, the title compound was prepared. Purification by flash chromatography (2:1 ethyl acetate/hexanes) afforded the pure product.

$C_{27}H_{37}N_3O_7$ (MW=515.6); mass spectroscopy (MH⁺) 516.0.

Anal. Calcd for $C_{27}H_{37}N_3O_7$: C, 62.90; H, 7.23; N, 8.15. Found: C, 62.93; H, 7.39; N, 8.06.

Example 4

Synthesis of Methyl N-(2-N'-(N''-benzyloxycarbamoyl-L-phenylglycine)ethyl)-N'-2-t-butylcarbamoylethyl amine

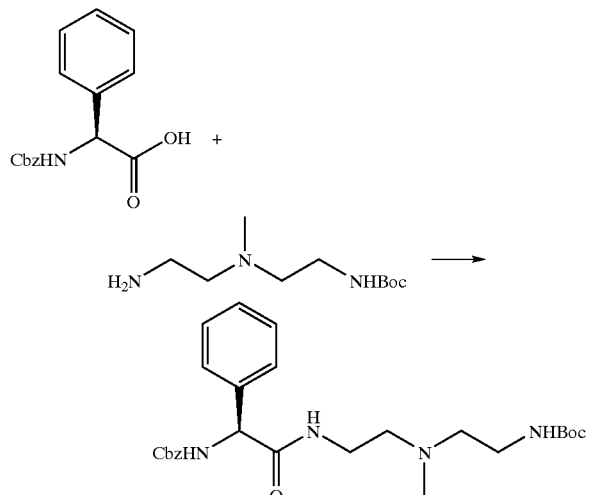

Following general procedure B and using N-Cbz-L-phenylglycine (Bachem) as the carboxylic component and methyl N-2-aminoethyl-N'-2-t-butylcarbamoylethyl amine (from Example 2 above) as the amine component, the title compound was prepared. Purification by flash chromatography (5:1 ethyl acetate/methanol) afforded the pure product.

$C_{26}H_{36}N_4O_5$ (MW=484.6); mass spectroscopy (MH⁺) 485.6.

Anal. Calcd for $C_{26}H_{36}N_4O_5$: C, 64.44; H, 7.49; N, 11.56. Found: C, 64.33; H, 7.24; N, 10.75.

Example 5

Synthesis of tert-butyl N-(2-N'-(N''-benzyloxycarbonyl-L-phenylglycine)ethyl) carbamate

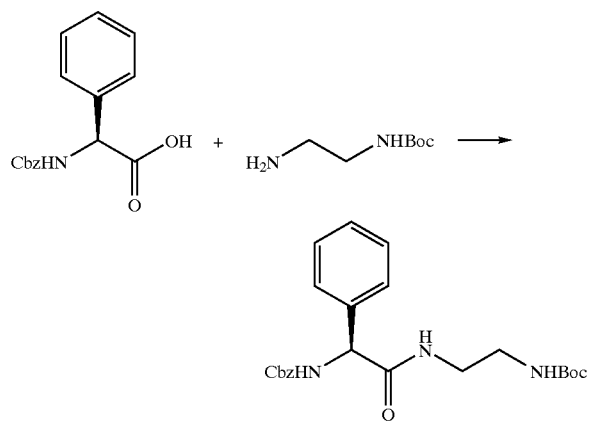

Following general procedure E and using N-Cbz-L-phenylglycine (Bachem) as the carboxylic component and tert-butyl-N-(2-aminoethyl) carbamate (Fluka) as the amine component, the title compound was prepared. Purification by flash chromatography (9:1 methylene chloride/methanol) afforded the pure product.

$C_{23}H_{29}N_3O_5$ (MW=427.5); mass spectroscopy (MH⁺) 428.2

Anal. Calcd for $C_{23}H_{29}N_3O_5$: C, 64.62; H, 6.84; N, 9.83. Found: C, 64.34; H, 6.61; N, 9.81.

Example 6

Synthesis of tert-butyl N-(8-N'-L-phenylglycine-3,6-dioxaoctyl) carbamate

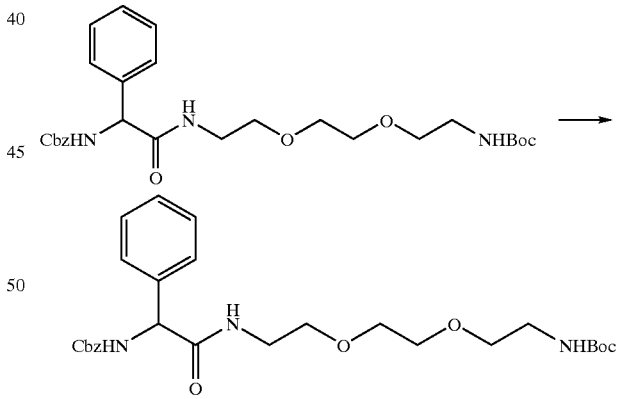

Following general procedure C and using tert-butyl N-(8-N'-(N''-benzyloxycarbonyl-L-phenylglycine)-3,6-dioxaoctyl) carbamate (set forth in Example 3) as the substrate, the title compound was prepared. Purification by flash chromatography (3:1 ethyl acetate/methanol) afforded the pure product.

$C_{19}H_{31}N_3O_5$ (MW=381.5); mass spectroscopy (MH⁺) 382.4

NMR data was as follows:
¹H-nmr (CD₃OD, 250 MHz) δ=7.47–7.24 (m, 5H), 4.47 (s, 1H), 3.60–3.16 (m, 12H), 1.44 (s, 9H)

Example 7

Synthesis of Methyl N-(2-N-(L-phenylglycine)ethyl)-N'-2-t-butylcarbamoylethyl amine

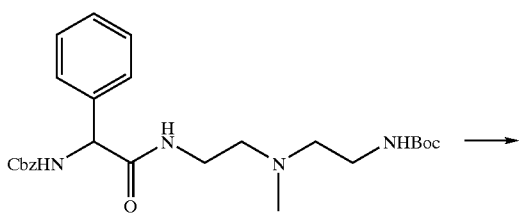

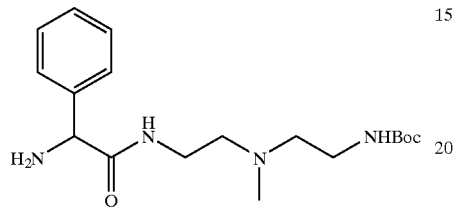

Following general procedure C and using methyl N-(2-N'-(N''-benzyloxycarbamoyl-L-phenylglycine)ethyl)-N'-2-t-butylcarbamoylethyl amine (set forth in Example 4 above) as the substrate, the title compound was prepared. Purification by flash chromatography (5:1 ethyl acetate/methanol) afforded the pure product.

$C_{18}H_{30}N_4O_3$ (MW=350.5); mass spectroscopy (MH$^+$) 351.5

Anal. Calcd for $C_{18}H_{30}N_4O_3$: C, 61.69; H, 8.63; N, 15.99. Found: C, 61.63; H, 8.52; N, 15.85.

Example 8

Synthesis of tert-butyl N-(2-N'-L-phenylglycine)-ethyl carbamate

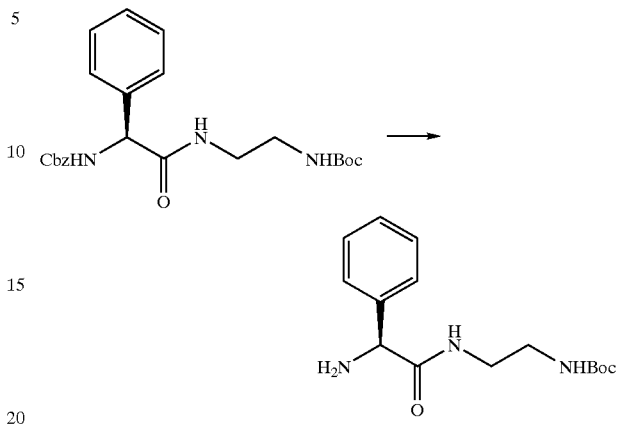

Following general procedure C and using tert-butyl N-(2-N'-(N''-benzyloxycarbonyl-L-phenylglycine)-ethyl) carbamate (as set forth in Example 5 above) as the substrate, the title compound was prepared. Purification by flash chromatography (10:1 to 5:1 ethyl acetate/methanol gradient) afforded the pure product.

$C_{15}H_{23}N_3O_3$ (MW=293.37); mass spectroscopy (MH$^+$) 294.3

Anal. Calcd for $C_{15}H_{23}N_3O_3$: C, 61.41; H, 7.90; N, 14.32. Found: C, 61.18; H, 7.98; N, 14.09.

Example 9

Synthesis of tert-butyl N-[8-N'-((2-(R/S)-hydroxy-2-(3,5-difluorophenyl)-acetyl-L-alaninyl)-L-phenylglycine) 3,6-dioxaoctyl] carbamate

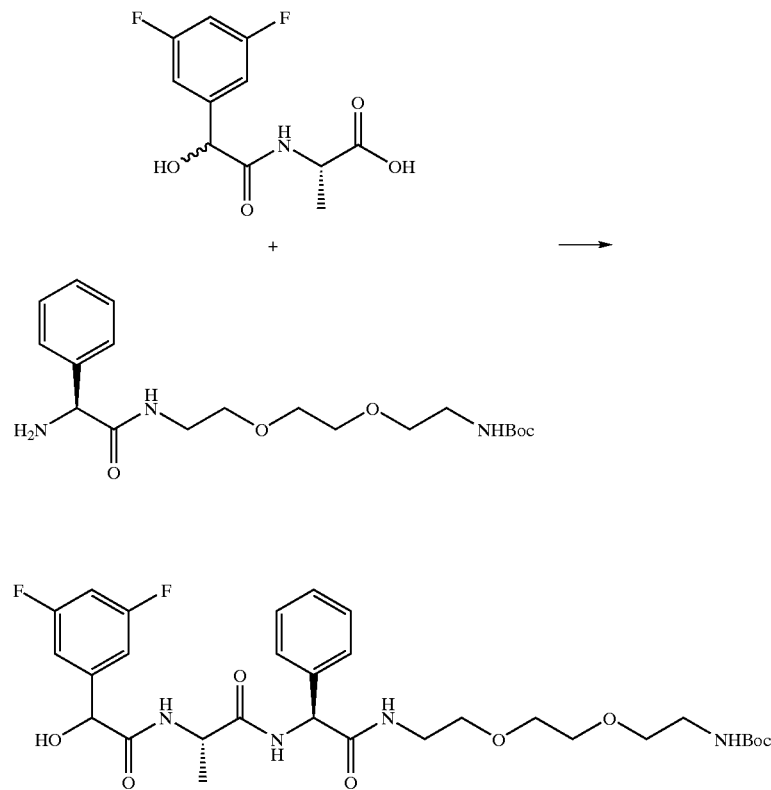

Following general procedure B and using N-((R/S)-3,5-difluorophenyl-α-hydroxyacetyl)-L-alanine (as set forth in Example 15 below) as the carboxylic component and tert-butyl N-(8-N'-L-phenylglycine-3,6-dioxaoctyl) carbamate (set forth in Example 6 above) as the amine component, the title compound was prepared. Purification by flash chromatography (10:1 ethyl acetate/methanol) afforded the pure product.

$C_{30}H_{40}F_2N_4O_8$ (MW=622.67); mass spectroscopy (MH$^+$)=623.5

Anal. Calcd for $C_{30}H_{40}F_2N_4O_8$: C, 57.87; H, 6.48; N, 9.00. Found: C, 57.86; H, 6.30; N, 8.86.

Example 10

Synthesis of Methyl N-[2-N-((2-(R/S)-hydroxy-2-(3,5-difluorophenyl)-acetyl-L-alaninyl)-L-phenylglycine)ethyl]-N'-2-t-butylcarbamoylethyl amine

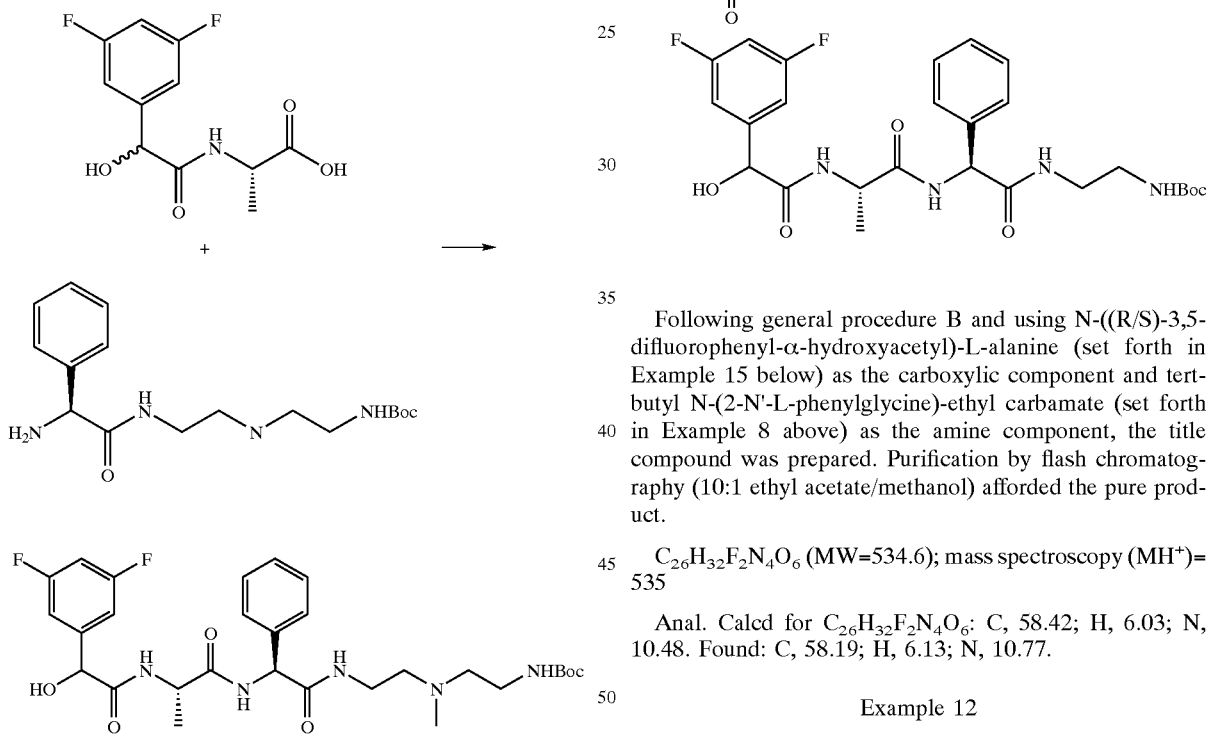

Following general procedure B and using N-((R/S)-3,5-difluorophenyl-a-hydroxyacetyl)-L-alanine (set forth in Example 15 below) as the carboxylic component and methyl N-(2-N-(L-phenylglycine)ethyl)-N'-2-t-butylcarbamoyl-ethyl amine (set forth in Example 7 above) as the amine component, the title compound was prepared. Purification by flash chromatography (5:1 ethyl acetate/methanol) afforded the pure product.

$C_{29}H_{39}F_2N_5O_6$ (MW=591.7); mass spectroscopy (MH$^+$)=592.7

Anal. Calcd for $C_{29}H_{39}F_2N_5O_6$: C, 58.87; H, 6.64; N, 11.84. Found: C, 57.47; H, 6.59; N, 11.68.

Example 11

Synthesis of tert-butyl N-[2-N'-((2-(R/S)-hydroxy-2-(3,5-difluorophenyl)-acetyl-L-alaninyl)-L-phenylglycine)-ethyl]carbamate

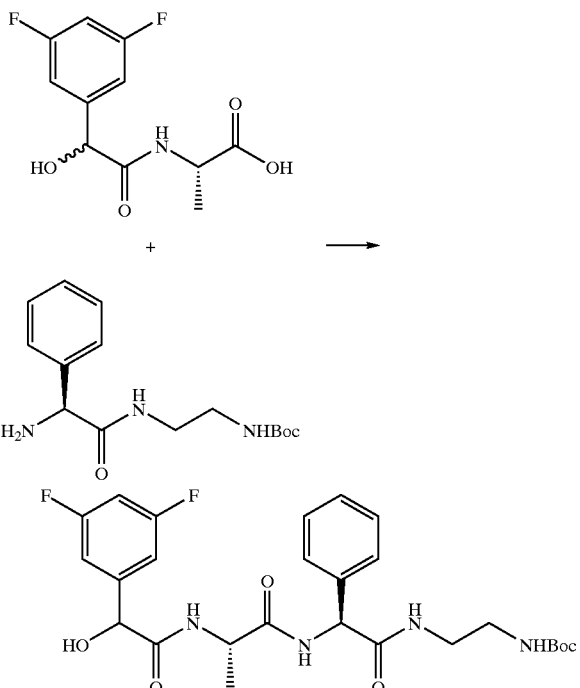

Following general procedure B and using N-((R/S)-3,5-difluorophenyl-α-hydroxyacetyl)-L-alanine (set forth in Example 15 below) as the carboxylic component and tert-butyl N-(2-N'-L-phenylglycine)-ethyl carbamate (set forth in Example 8 above) as the amine component, the title compound was prepared. Purification by flash chromatography (10:1 ethyl acetate/methanol) afforded the pure product.

$C_{26}H_{32}F_2N_4O_6$ (MW=534.6); mass spectroscopy (MH$^+$)=535

Anal. Calcd for $C_{26}H_{32}F_2N_4O_6$: C, 58.42; H, 6.03; N, 10.48. Found: C, 58.19; H, 6.13; N, 10.77.

Example 12

Synthesis of Tert-butyl-2-(2'-(N'-benzyloxycarbonyl-L-phenylglycine)aminoethoxy) ethylcarbamate

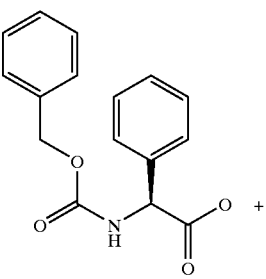

-continued

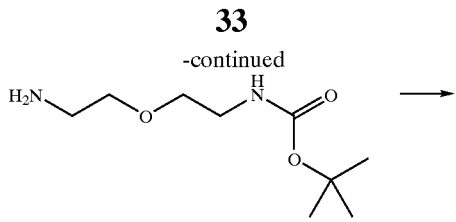

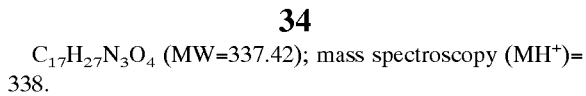

$C_{17}H_{27}N_3O_4$ (MW=337.42); mass spectroscopy (MH$^+$)= 338.

Anal. calcd. For $C_{17}H_{27}N_3O_4$: C, 60.51; H, 8.07; N, 12.45. Found: C, 59.12; H, 7.86; N, 12.26.

Example 14

Synthesis of N-((R/S)-3,5-difluorophenyl-α-hydroxyacetyl)-L-alanine, methyl ester

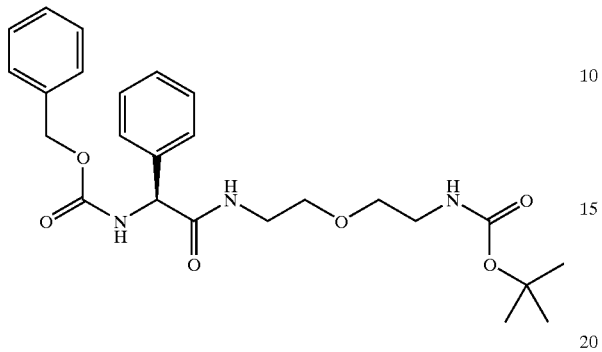

Following General Procedure E and using tert-butyl-2-(2'-aminoethoxy)ethylcarbamate (as described in *Bioconjugate Chem.* (1990), 1 (6), 431–437[12]) and benzyloxycarbonyl-L-phenylglycine (Aldrich) the title compound was made.

$C_{25}H_{35}N_3O_6$ (MW=473.57); mass spectroscopy (MH$^+$)= 474.

Anal. Calcd. For $C_{25}H_{35}N_3O_6$, C, 63.41; H, 7.45; N, 8.87; Found: C, 63.09; H, 7.13; N, 8.56.

Example 13

Synthesis of Tert-butyl-2-(2'-(L-phenylglycine) aminoethoxy)ethylcarbamate.

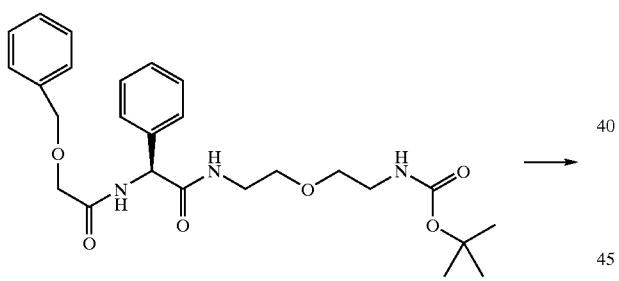

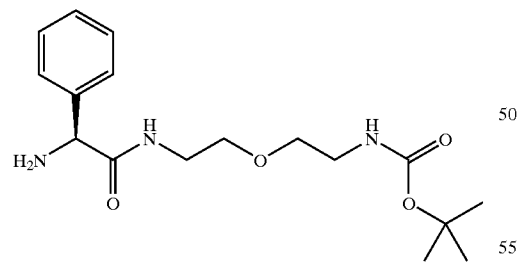

Tert-butyl-2-(2'-(N'-benzyloxycarbonyl-L-phenylglycine) aminoethoxy)ethylcarbamate, (as set forth in Example 12 above), was suspended in MeOH at room temperature under a nitrogen atmosphere. 5% Pd/C, 25 mg catalyst/1 mmol substrate, was added under nitrogen, and the reaction mixture was stirred under a hydrogen atmosphere (balloon) for 17 hours. The mixture was filtered through celite, and the solvents removed in vacuo. The residue was purified via radial chromatography using 50% ethyl acetate in acetonitrile to afford the title compound.

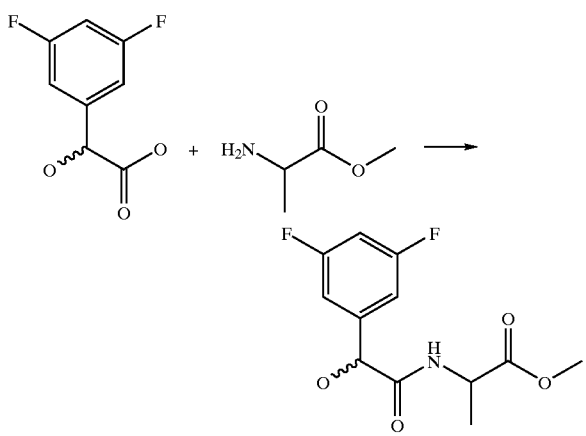

Following General Procedure E and using (R/S)-3,5-difluoromandelic acid (as set forth in General Procedure H, step A) and L-alanine, methyl ester (Bachem) the title compound was synthesized.

$C_{12}H_{13}F_2NO_4$ (MW=273.23) mass spectroscopy (M+) 273.

NMR data was as follows:

$^1$H-nmr (400 MHz, CDCl$_3$) δ=7.03–6.76 (3H, m), 5.08 (1H, s), 4.61–4.54 (1H, m), 3.75 (3H, s), 1.43 (3H, d, J=5.6 Hz).

Example 15

Synthesis of N-((R/S-3,5-difluorophenyl-α-hydroxyacetyl)-L-alanine

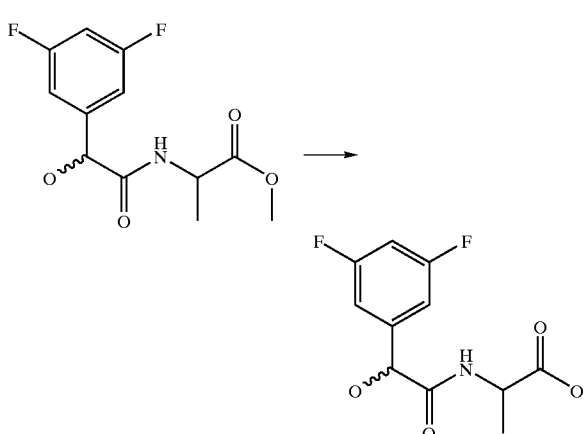

Following General Procedure F, Method B and using N-((R/S)-3,5-difluorophenyl-α-hydroxyacetyl)-L-alanine, methyl ester (set forth in Example 14 above) afforded the title compound.

$C_{11}H_{11}F_2NO_4$ (MW=259.21); mass spectroscopy (MH$^+$)=260.

NMR data was as follows:

$^1$H-nmr (400 MHz, CDCl$_3$) δ=7.02–7.00 (2H, m), 6.80–6.76 (1H, m), 5.11 (1H, s), 4.61–4.52 (1H, m), 1.48 (3H, d, J=5.2 Hz).

Example 16

Synthesis of tert-butyl-2-(2'-(N'-(((R/S)-3,5-difluorophenyl-α-hydroxyacetyl)-L-alanine)-L-phenylglycine)aminoethoxy)ethylcarbamate

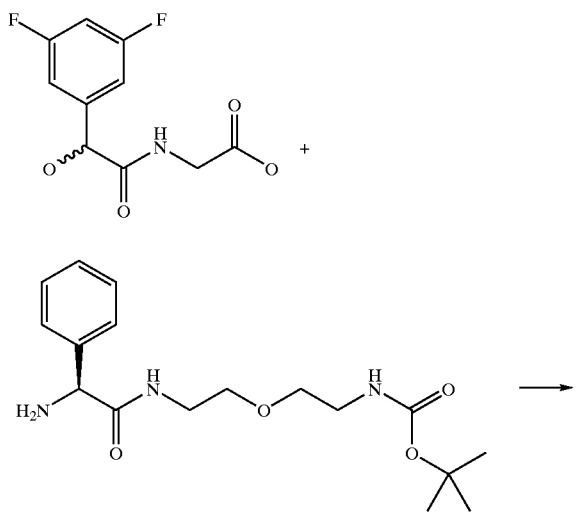

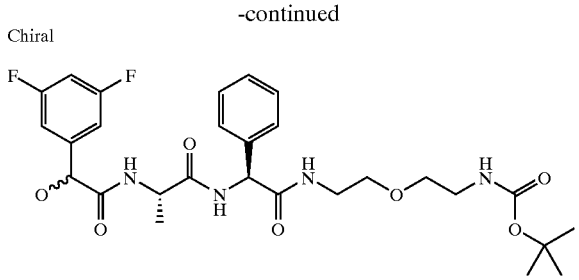

Chiral

Following General Procedure E and using N-((R/S)-3,5-difluorophenyl-α-hydroxyacetyl)-L-alanine (set forth in Example 15 above) and tert-butyl-2-(2'-(L-phenylglycine)aminoethoxy)ethylcarbamate (set forth in Example 13 above), the title intermediate was synthesized.

$C_{28}H_{36}F_2N_4O_7$ (MW=578.61); mass spectroscopy (MH$^+$)=579.

NMR data was as follows:

$^1$H-nmr (400 MHz, CDCl$_3$) δ=8.01–8.58 (1H, m), 7.41–7.23 (5H, m), 7.10–6.96 (2H, m), 6.75–6.65 (1H, m), 5.63–5.50 (1H, m), 5.17–5.05 (1H, m), 4.78–4.62 (1H, m), 3.49–2.25 (6H, m), 3.22–3.16 (2H, m), 1.50 (9H, s), 1.37 (3H, d, J=5.7 Hz).

Example 17

Synthesis of 8-N'-((2-(R/S)-hydroxy-2-(3,5-difluorophenyl)-acetyl-L-alaninyl)-L-phenylglycinyl)amino-3,6dioxaoctylamine hydrochloride

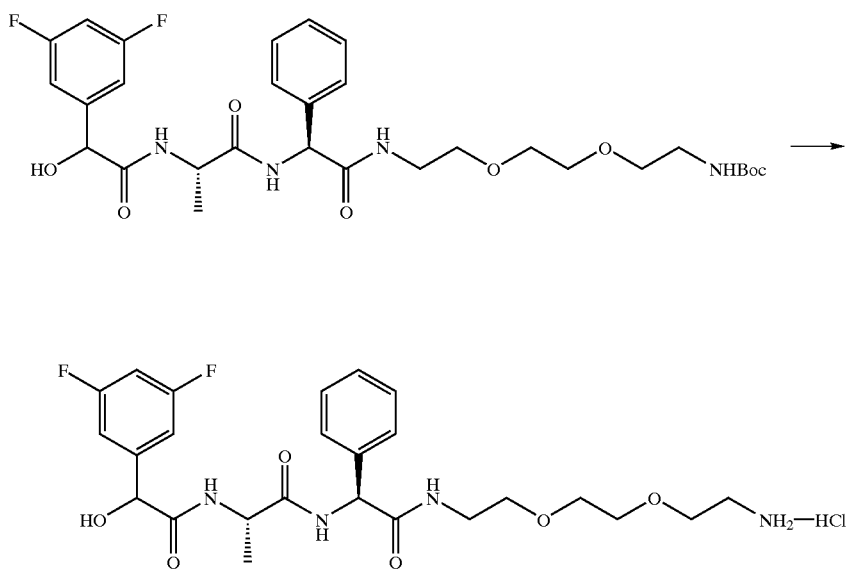

Following general procedure D and using tert-butyl N-[8-N'-((2-(R/S)-hydroxy-2-(3,5-difluorophenyl)-acetyl-L-alaninyl)-L-phenylglycine)-3,6-dioxaoctyl] carbamate (set forth in Example 9 above) as the substrate, the title compound was prepared.

$C_{25}H_{32}F_2N_4O_6$—HCl (MW=558.2); mass spectroscopy (MH⁺)=557.1

Anal. Calcd for $C_{25}H_{32}F_2N_4O_6$—HCl: C, 53.72; H, 5.95; N, 10.02. Found: C, 49.63; H, 5.68; N, 8.37.

Example 18

Synthesis of Methyl N-[2-N-((2-(R/S)-hydroxy-2-(3,5-difluorophenyl)-acetyl-L-alaninyl)-L-phenylglycinyl)aminoethyl]-N'-2-aminoethyl amine hydrochloride

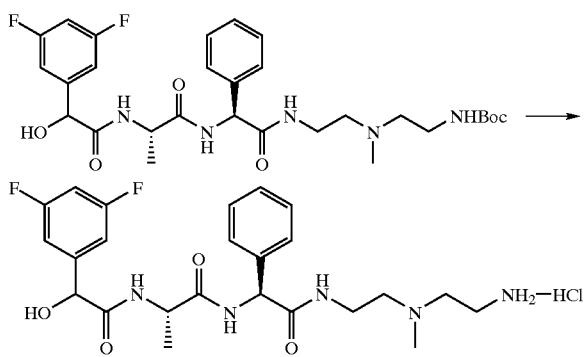

Following general procedure D and using methyl N-[2-N-((2-(R/S)-hydroxy-2-(3,5-difluorophenyl)-acetyl-L-alaninyl)-L-phenylglycine)ethyl]-N'-2-t-butylcarbamoyl-ethyl amine (set forth in Example 10 above) as the substrate, the title compound was prepared.

$C_{24}H_{31}F_2N_5O_4$—HCl (MW=528.0); mass spectroscopy (MH⁺)=526.3

NMR data was as follows:

¹H-nmr (CD₃OD, 250 MHz) δ7.51–7.29 (m, 5H), 7.22–7.04 (m, 2H), 7.00–6.87 (m, 1H), 5.33–5.09 (m, 2H), 4.49–4.33 (m, 1H), 3.79–3.36 (m, 8H), 3.07–2.96 (m, 3H), 1.27–1.36 (m, 3H).

Example 19

Synthesis of 2-N'-((2-(R/S)-hydroxy-2-(3,5-difluorophenyl)-acetyl-L-alaninyl)-L-phenylglycine)-ethylamine hydrochloride

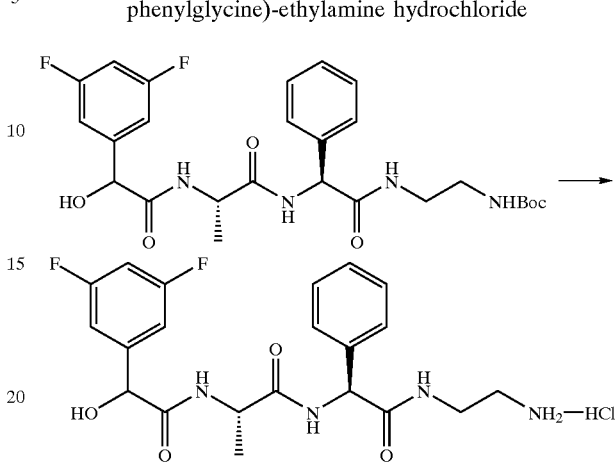

Following general procedure D and using tert-butyl N-[2-N'-((2-(R/S)-hydroxy-2-(3,5-difluorophenyl)-acetyl-L-alaninyl)-L-phenylglycine)-ethyl] carbamate (set forth in Example 11 above) as the substrate, the title compound was prepared.

$C_{21}H_{24}F_2N_4O_4$—HCl (MW=470.9); mass spectroscopy (MH⁺)=469.2

Anal. Calcd for $C_{21}H_{24}F_2N_4O_4$—HCl: C, 53.56; H, 5.35; N, 11.90.

Found: C, 54.58; H, 5.65; N, 10.99.

Example 20

Synthesis of N-(8-N'-((2-(R/S)-hydroxy-2-(3,5-difluorophenyl)-acetyl-L-alaninyl)-L-phenylglycine)-3,6-dioxaoctyl)-biotinamide

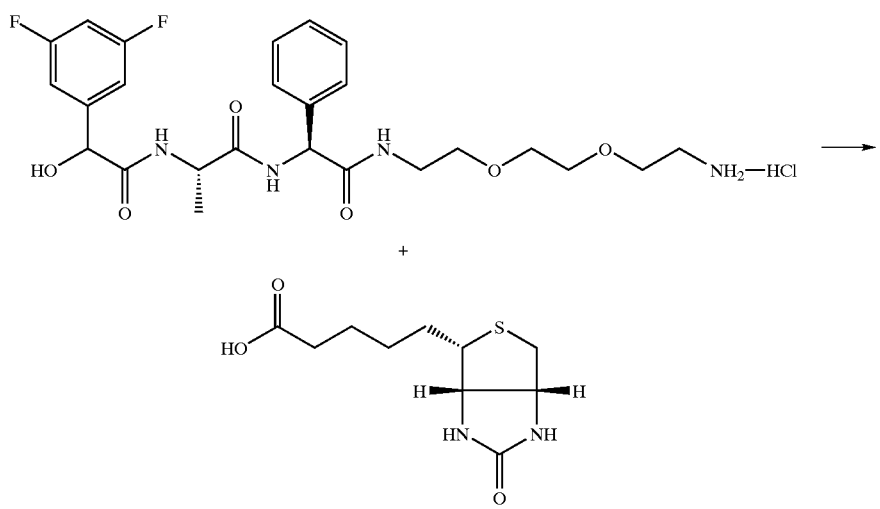

-continued

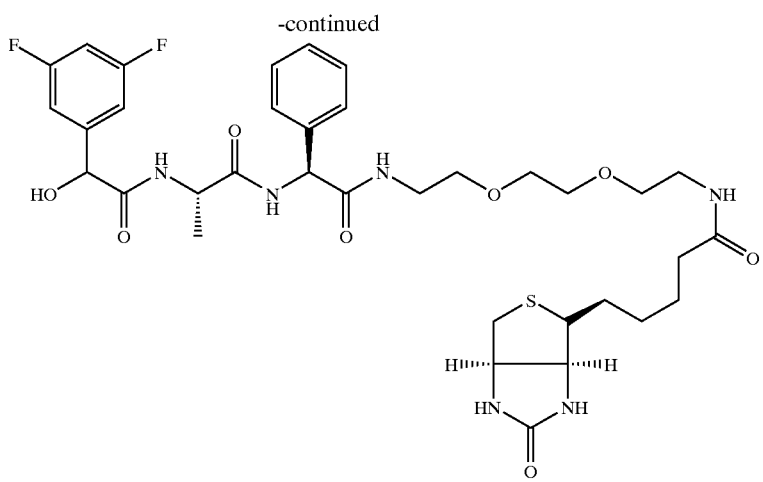

General procedure B was used with the exception that dimethylformamide was used in place of tetrahydrofuran and 2 eq. diisopropylethylamine was added to the reaction mixture. Using d-biotin (Sigma) as the carboxylic acid component and 8-N'-((2-(R/S)-hydroxy-2-(3,5-difluorophenyl)-acetyl-L-alaninyl)-L-phenylglycine)-3,6-dioxaoctylamine hydrochloride (set forth in Example 17 above) as the amine component, the title compound was prepared. Purification by flash chromatography (3:1 ethyl acetate/methanol) afforded the pure product.

$C_{35}H_{46}F_2N_6O_8S$ (MW=748.9); mass spectroscopy (MH$^+$)=749.3

Anal. Calcd for $C_{35}H_{46}F_2N_6O_8S$: C, 56.14; H, 6.19; N, 11.22. Found: C, 55.45; H, 6.33; N, 10.85.

Example 21

Synthesis of 2-(2'-(N'-(((R/S)-3,5-difluorophenyl-α-hydroxyacetyl)-L-alanine)-L-phenylglycine)aminoethoxy)ethylamine, hydrochloride salt

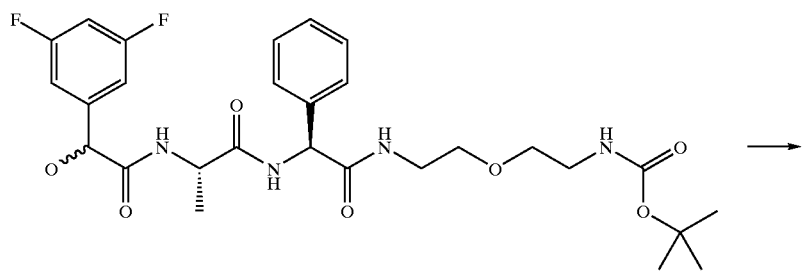

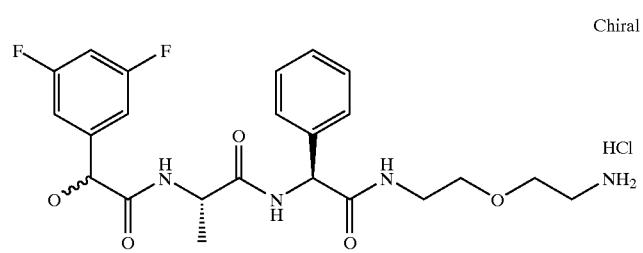

Following General Procedure G using no cooling bath, and using tert-butyl-2-(2'-(N'-(((R/S)-3,5-difluorophenyl-α-hydroxyacetyl)-L-alanine)-L-phenylglycine)aminoethoxy)ethylcarbamate (set forth in Example 16), the title compound was prepared.

$C_{23}H_{28}F_2N_4O_5 \cdot Cl\, H$ (MW=478.50); mass spectroscopy (MH$^+$)=479.

NMR data was as follows:

$^1$H-nmr (400 MHz, CD$_3$OD) δ=7.42–7.30 (5H, m), 7.18–7.05 (2H, m), 6.99–6.82 (1H, m), 5.40–5.22 (1H, m), 5.06 (1H, d, J=9.8 Hz), 4.50–4.36 (1H, m), 3.60–3.23 (6H, m), 3.01 (2H, br s), 1.40–1.32 (3H, d, J=6.1 Hz).

Example 22

Synthesis of 1-[N-(3,5-difluorophenylacetyl)-L-alaninyl)-(L-phenylglycinyl)]amino-6-(N-biotinyl)aminohexane

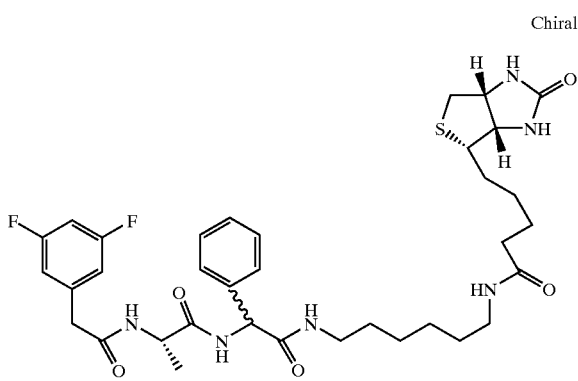

Following General Procedure E and General Procedure G and using biotin and tert-butyl N-(6-aminohexyl)carbamate hydrochloride (Fluka), N-biotinyl-1,6-hexanediamine hydrochloride was prepared. The free base form was obtained by purification using SCX-silica gel chromatography.

Step 2

Following General Procedure E and using N(3,5-difluorophenylacetyl)-L-alaninyl-phenylglycine (Example D25 of International Patent Application No. PCT/US98/20804[11]) and N-biotinyl-1,6-hexanediamine hydrochloride (prepared in Step 1 above), the title compound was prepared.

$C_{35}H_{46}F_2N_6O_5S$ (MW 700.855); mass spectroscopy (MH$^+$)=701.

NMR data was as follows:

$^1$H-nmr ($\delta^6$-DMSO) $\delta$=5.40(t,1H); 6.36(s,1H); 6.43(s, 1H).

Example 23

Synthesis of 1-[N-(3,5-difluorophenylacetyl)-L-alaninyl)-(L-phenylglycinyl)]amino-3-(4-iodophenoxy)propane

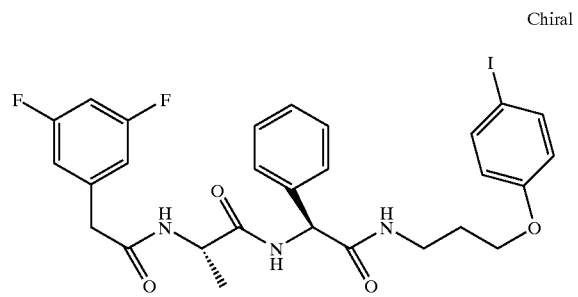

Step 1

N-(3-bromopropyl)phthalimide (1 eq., Aldrich), 4-iodophenol (1 eq., Aldrich) and potassium carbonate (2 eq.) were stirred in acetonitrile. The mixture was heated at reflux. After 64 hours, the reaction mixture was concentrated to a thick mixture which was slurried in water. A white solid was collected, washed with water and vacuum dried to provide 1-(4-iodophenoxy)-3-(phthalimido)propane.

mass spectroscopy (MH$^+$)=407.

Step 2

1-(4-Iodophenoxy)-3-(phthalimido)propane was stirred in ethanol. Anhydrous hydrazine (2 eq.) was added and the mixture was heated at reflux for 18 hours. The reaction mixture was concentrated to yield a solid which was treated with 1N NaOH and extracted with CHCl$_3$. The organic portion was dried, concentrated then diluted with ether. The mixture was treated with dry HCl. A white solid was collected and vacuum dried to provide 1-amino-3-(4-iodophenoxy)propane hydrochloride.

mass spectroscopy (MH$^+$)=277.

Step 3

Following General Procedure E and using N-t-Boc-phenylglycine (Advanced Chemtech) and 1-amino-3-(4-iodophenoxy)propane hydrochloride, 1-(N-t-Boc-phenylglycinyl)amino-3-(4-iodophenoxy)propane was prepared.

Step 4

Following General Procedure G and using 1-(N-t-Boc-phenylglycinyl)amino-3-(4-iodophenoxy)propane, 1-(phenylglycinyl)amino-3-(4-iodophenoxy)propane hydrochloride was prepared.

Step 5

Synthesis of N-(3,5-Difluorophenylacetyl)-L-alanine

Following the procedure set forth in Example B2 of International Patent Application No. PCT/US97/20804, 3,5-difluorophenylacetic acid (30 g, 0.174 mol) (Aldrich) was dissolved in dichloromethane and this solution was cooled to 0° C. DMF (0.5 mL, catalytic) was added followed by the dropwise addition of oxalyl chloride (18 mL, 0.20 mol) over a 5 minute period. The reaction was stirred for 3 h and then rotoevaporated at reduced pressure to a residue which was placed on a high vacuum pump for 1 h to afford 3,5-difluorophenylacetyl chloride as a thin yellow oil.

3,5-Difluorophenylacetyl chloride was added dropwise to a 0° C. solution of L-alanine (Aldrich) (16.7 g, 0.187 mol) in 2 N sodium hydroxide (215 mL, 0.43 mol). The reaction was stirred for 1 h at 0° C. and then overnight at room temperature. The reaction was diluted with water (100 mL), then extracted with ethyl acetate (3×150 mL). The organic layer was then washed with brine (200 mL), dried over MgSO$_4$, and rotoevaporated at reduced pressure to a residue. Recrystallization of the residue from ethyl acetate/hexanes afforded the desired product (34.5 g, 82% yield).

NMR data was as follows:

$^1$H-nmr (CD$_3$OD): $\delta$=8.32 (br s, 0.3H), 6.71 (m, 2H), 6.60 (m, 1H), 4.74 (br s, 1.7H), 4.16 (m, 1H), 3.36 (s, 2H), 1.19 (d, J=7.3 Hz, 3H).

$^{13}$C-nmr (CD$_3$OD): $\delta$=175.9, 172.4, 164.4 (dd, J=13.0, 245.3 Hz), 141.1, 113.1 (dd, J=7.8, 17.1 Hz), 102.9 (t, J=25.7 Hz), 49.5, 42.7, 17.5.

Step 6

Following General Procedure E and using N-(3,5-difluorophenylacetyl)-L-alanine (from step 5 above) and 1-(phenylglycinyl)amino-3-(4-iodophenoxy)propane hydrochloride (from step 4 above), the title compound was prepared.

mass spectroscopy (MH$^+$)=635.

Calc: C, 68.62; H, 6.16; N, 8.28. Found: C, 68.50; H, 6.04; N, 8.01.

Example 24

Synthesis of 1-[N-(3,5-difluorophenylacetyl)-L-alaninyl)-(L-phenylglycinyl)]amino-6-[N-(4-amino-7-nitrobenzofurazanyl)]hexane

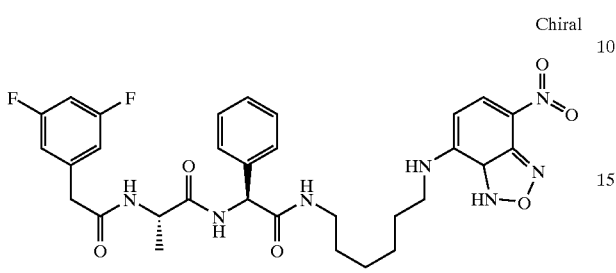

N-biotinyl-1,6-hexanediamine (as set forth in Example 22, Step 1)(1 eq.), 4-chloro-7-nitrobenzofurazan (2 eq., Aldrich), and triethylamine (2 eq.) were stirred in DMF for 16 hours. The resulting mixture was concentrated to yield a crude solid which was purified by silica gel chromatography to yield the title compound.

$C_{31}H_{35}F_2N_7O_6$ (MW 639.66); mass spectroscopy (MH$^+$)=638.3.

NMR data was as follows:

$^1$H-nmr ($\delta^6$-DMSO) $\delta$5.37(d,1H); 6.37(d,1H)

Rf (5% methanol/methylene chloride)=0.2.

Example 25

Synthesis of 1-[N-(3,5-difluorophenylacetyl)-L-alaninyl)-(L-phenylglycinyl)]amino-3-(4-trimethylstannylphenoxy)propane

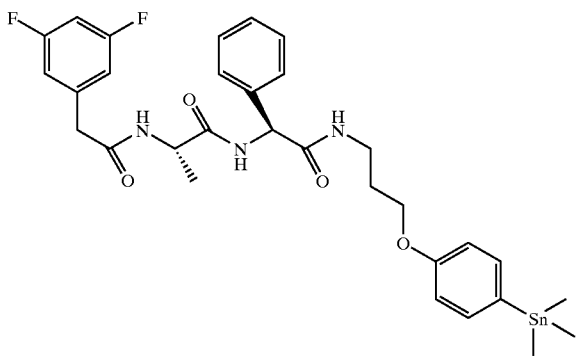

1-[N-(3,5-difluorophenylacetyl)-L-alaninyl)-(L-phenylglycinyl)]amino-3-(4-iodophenoxy)propane (as set forth in Example 23) (1 eq.), hexamethylditin (2 eq.), and tetrakis(triphenylphosphine)palladium(Aldrich) (0.1 eq) were stirred in 1,4-dioxane. The mixture was heated at reflux for 16 hours. The mixture was allowed to cool then was diluted with methylene chloride and filtered through Celite. The filtrate was concentrated to provide a crude product which was purified by silica gel chromatography.

NMR data was as follows:

$^1$H-NMR ($\delta^6$-DMSO) $\delta$=4.28(m,1H); 5.25(d,1H)

Rf (10% methanol/methylene chloride)=0.5.

Example 26

Synthesis of N-{1-N-[N-(3,5-difluorophenylacetyl)-L-alaninyl-(L-phenylglycinyl)amino-6hexyl]}-4,4-difluoro-5,7-dimethyl-4-bora-3α,4αdiaza-s-indacene-3-propionamide

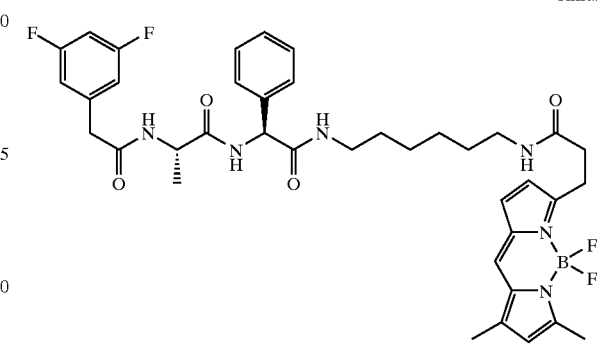

Step 1

Following General Procedure E and using Cbz-L-phenylglycine (Advanced Chemtech) and N-t-Boc-1,6-hexanediamine (Fluka), 1-N-(Cbz-L-phenylglycinyl)-6-(N-t-Boc)-hexanediamine was prepared.

Step 2

1-N-(Cbz-L-phenylglycinyl)-6-(N-t-Boc)-hexanediamine was stirred in ethanol with 5% palladium on carbon under an atmosphere of hydrogen (60 psi) at ambient temperature for 16 hours. The mixture was filtered and the filtrate was concentrated to provide 1-N-(L-phenylglycinyl)-6-(N-t-Boc) hexanediamine.

Step 3

Following General Procedure E and using N-(3,5-difluorophenylacetyl)-L-alanine and 1-N-(L-phenylglycinyl)-6-(N-t-Boc)-hexanediamine, 1-N-[N-(3,5-difluorophenylacetyl)-L-alaninyl-(L-phenylglycinyl)-6-(N-t-Boc)-hexanediamine was prepared.

Step 4

Following General Procedure G and using 1-N-[N-(3,5-difluorophenylacetyl)-L-alaninyl-(L-phenylglycinyl)-6-(N-t-Boc)-hexanediamine, 1-N-[N-(3,5-difluorophenylacetyl)-L-alaninyl-(L-phenylglycinyl)-6-hexanediamine was prepared.

Step 5

Following General Procedure I and using 1-N-[N-(3,5-difluorophenylacetyl)-L-alaninyl-(L-phenylglycinyl)-6-hexanediamine, the title compound was prepared.

Rf (5% methanol/methylene chloride) 0.25.

Example 27

Synthesis of N-{methyl N-[2-N-((2-(R/S)-hydroxy-2-(3,5-difluorophenyl)-acetyl-L-alaninyl)-L-phenylglycinyl)aminoethyl]-N'-2-aminoethyl}4,4-difluoro-5,7-dimethyl-4-bora-3α,4α-diaza-s-indacene-3-propionamide

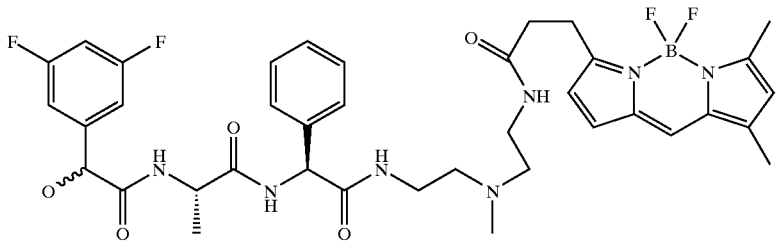

Following General Procedure I and using methyl N-[2-N-((2-(R/S)-hydroxy-2-(3,5-difluorophenyl)-acetyl-L-alaninyl)-L-phenylglycinyl)aminoethyl]-N'-2-aminoethyl amine hydrochloride (as set forth in Example 18), the title compound was prepared.

Mass Spectroscopy (MH+)=766.1.

Example 28

Synthesis of N-[8-N'-((2-(R/S)-hydroxy-2-(3,5-difluorophenyl)-acetyl-L-alaninyl)-L-phenylglycinyl)amino-3,6-dioxaoctyl]-4,4-difluoro-5,7-dimethyl-4-bora-3α,4α-diaza-s-indacene-3-propionamide

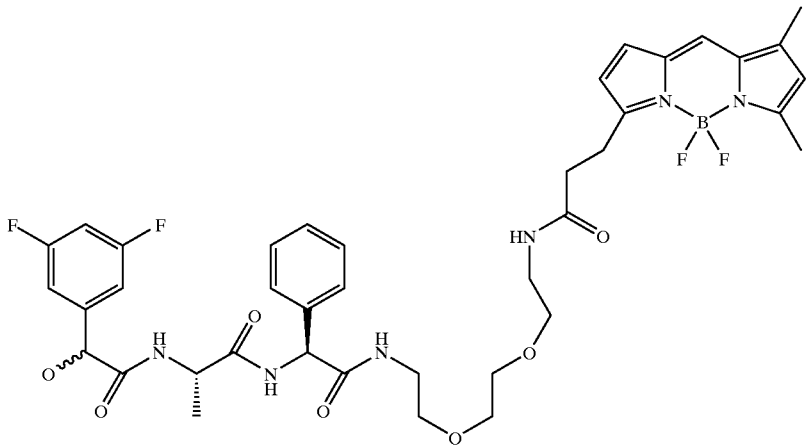

Following General Procedure I and using 8-N'-((2-(R/S)-hydroxy-2-(3,5-difluorophenyl)-acetyl-L-alaninyl)-L-phenylglycinyl)amino-3,6-dioxaoctylamine hydrochloride (as set forth in Example 17), the title compound was prepared. The title compound contains the C-terminal fluorophore, coupled via its succinimidyl ester, 4,4-difluoro-5,7-dimethyl-4-bora-3α,4α-diaza-s-indacene-3-propionic acid. The ester is coupled via the C-terminal amine of abis-ethylene amine ethylene glycol linker attached to the C-terminal nitrogen of the dipeptide difluoromandelate-ala-phenyl gly.

Mass Spectroscopy (MH+)=797.2.

Example 29

Synthesis of 5-(S)-[N'-((S)-3,5-Difluorophenyl-α-hydroxyacetyl)-L-alaninyl]amino-7-methyl-5,7-dihydro-6H-dibenz[b,d]azepin-6-one and 5-(S)-[N'-((R)-3,5-Difluorophenyl-α-hydroxyacetyl)-L-alaninyl]amino-7-methyl-5,7-dihydro-6H-dibenz[b,d]azepin-6-one

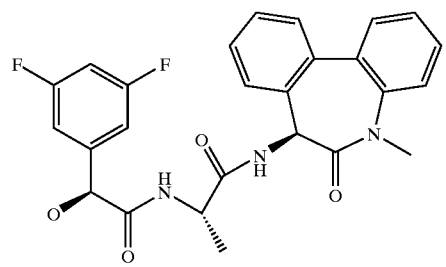

Following General Procedure D (from International Patent Application No. PCT/US97/22986[13]) above using 3,5-difluoromandelic acid and 5-(S)-[L-alaninyl]-amino-7-methyl-5,7-dihydro-6H-dibenz[b,d]azepin-6-one hydrochloride (Example 7-B of International Patent Application No. PCT/US97/22986), the title compound was prepared as a colorless solid. The diastereomers were purified by flash chromatography using 98:2 CHCl$_3$/MeOH.

Isomer 1:

NMR data was as follows:

$^1$H-nmr (CDCl$_3$): δ=7.67 (d, 1H), 7.60–7.28 (m, 8H), 7.15 (d, 1H), 6.98 (m, 2H), 6.74 (m,1H), 5.21 (d,1H), 4.94 (d,1H), 4.61 (m,1H), 4.56 (m, 1H), 3.34 (s, 3H), 1.42 (d, 3H).

Optical Rotation: [α]$_{20}$=–121 @ 589 nm (c=1, MeOH).

C$_{26}$H$_{23}$F$_2$N$_3$O$_4$ (MW=479.488); mass spectroscopy (MH+) 479.

Anal. Calcd for C$_{26}$H$_{23}$F$_2$N$_3$O$_4$; C, 65.13; H, 4.83; N, 8.76. Found: C, 65.42; H, 4.73; N, 8.65.

Isomer 2:

NMR data was as follows:

$^1$H-nmr (CDCl$_3$): δ=7.78 (d, 1H), 7.66 (d, 1H), 7.54–7.28 (m, 8H), 6.89 (m, 2H), 6.71 (m, 2H), 5.22 (d 1H), 4.92 (m,1H), 4.65 (m,1H), 4.01 (m, 1H), 3.37 (s, 3H), 1.39 (d, 3H).

Optical Rotation: [α]$_{20}$=–146 589 nm (c=1, MeOH).

C$_{26}$H$_{23}$F$_2$N$_3$O$_4$ (MW=479.488); mass spectroscopy (MH+) 479.

Anal. Calcd for C$_{26}$H$_{23}$F$_2$N$_3$O$_4$; C, 65.13; H, 4.83; N, 8.76. Found: C, 65.18; 4.82; 8.65.

Example 30

Synthesis of 5-(S)-(N'-((S)-(+)-2-Hydroxy-3-methylbutyryl)-L-alaninyl)amino-7-methyl-5,7-dihydro-6H-dibenz[b,d]azepin-6-one Chiral

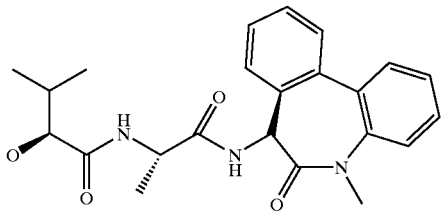

Following General Procedure H (from International Patent Application No. PCT/US98/22986[13]) using (S)-(+)-2-hydroxy-3-methylbutyric acid (Aldrich) and 5-S-(L-alaninyl)-amino-7-methyl-5,7-dihydro-6H-dibenz[b,d]azepin-6-one (Example 7-B from International Patent Application No. PCT/US98/22986[13]), the title compound was prepared as a white solid. The product was purified by silica gel chromatography using gradient elution of MeOH/CH$_2$Cl$_2$ (1:99–3:97).

NMR data was as follows:

$^1$H-nmr (CDCl$_3$): δ=7.94 (d, J=7.0 Hz, 1H), 7.55–7.22 (m, 9H), 5.25 (d, J=7.5 Hz, 1H), 4.79–4.75 (m, 1H), 3.83 (d, J=3.1 Hz, 1H), 3.78 (br s, 1H), 3.32 (s, 3H), 2.08–2.01 (m, 1H), 1.36 (d, J=7.0 Hz, 3H), 0.83 (d, J=7.0 Hz, 3H), 0.76 (d, J=6.5 Hz, 3H).

C$_{23}$H$_{27}$N$_3$O$_4$ (MW=409.48); mass spectroscopy (MH$^+$) 410.4.

Anal Calcd for C$_{23}$H$_{27}$N$_3$O$_4$, C, 67.46; H, 6.65; N, 10.26; Found: C, 67.59; H, 6.66; N, 10.34.

Example 31

Synthesis of Azido Compound 1-[N-(3,5-difluorophenylacetyl)-L-alaninyl)-(L-phenylglycinyl)]amino-4-p-azidosalicylamidobutane

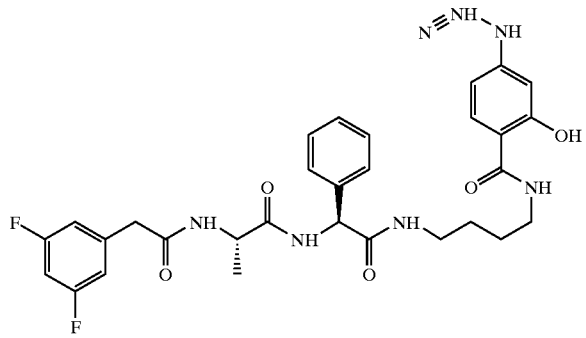

The title compound was made with 4-(p-azidosalicylamido)butylamine (Pierce) and N-3,5-difluorophenylacetyl-alaninyl-phenylglycine according to the following method except DMF was used in place of CH$_2$CL$_2$.

To a 1:1 mixture of the corresponding carboxylic acid and the corresponding amino acid ester or amide in CH$_2$CL$_2$ at 0° C. was added 1.5 equivalents triethylamine, followed by 2.0 equivalents hydroxybenzotriazole monohydrate and then 1.25 equivalents of ethyl-3(3-dimethylamino propyl carbodiimide-HCl. The reaction mixture was stirred overnight at room temperature and then transferred to a separatory funnel. The mixture was washed with water, saturated aqueous NaHCO$_3$, 1N HCl and saturated aqueous NaCl, and then dried over MgSO$_4$. The resulting solution was stripped free of solvent on a rotary evaporator to yield the crude product.

NMR data was as follows:

$^1$H-nmr (CDCl$_3$ with 2 drops of CD$_3$OD, ppm): δ=1.35 (d,2H), 1.57 (bs, 4H), 3.21 (bs, 2H), 3.31 (bs, 2H), 3.56 (s, 2H), 4.39 (q, 1H), 5.34 (s, 1H), 6.54 (m, 2H), 6.73 (m, 1H), 6.84 (m, 2H), 7.30 (m, 5H), 7.72 (d, 2H) $^{13}$C-nmr (CDCl$_3$ with 2 drops of CD$_3$OD, ppm): δ=11.8, 21.6, 34.1, 34.2, 36.8, 44.7, 52.7, 97.3, 102.3, 105.1, 107.2, 107.5, 107.9, 122.5, 122.9, 123.5, 124.0, 124.6, 132.7, 140.6, 156.9, 164.5, 166.3, 166.8, 168.4, 168.8 C$_{30}$H$_{33}$F$_2$N$_7$O$_5$ (MW=609.64)

Example 32

Biological Assay

The pharmacological profile of $^3$H-5-(S)-(N'-((S)-(+)-2-Hydroxy-3-methylbutyryl)-L-alaninyl)amino-7-methyl-5,7-dihydro-6H-dibenz[b,d]azepin-6-one (Compound 1 from Example 30) has been studied in 293 membranes. There are two distinct binding components in the membrane preparations. Saturation binding analysis utilizing 0–50 pM and 0–150 nM $^3$H-Compound 1 reveal two sites (K$_D$1=52.7 pM [B$_{max}$1=710 fmol/mg protein]; K$_D$2=32.5 nM [B$_{max}$2=34.4 pmol/mg protein]).

The compound of Example 28 (Compound 3) was also tested. The high affinity $^3$H-N-[8-N'-((2-(R/S)-hydroxy-2-(3,5-difluorophenyl)-acetyl-L-alaninyl)-L-phenylglycine)-3,6- dioxaoctyl]-4,4-difluoro-5,7-dimethyl-4-bora-3α,4α-diaza-s-indacene-3-propionamide (Compound 3) binding site mediates the Aβ lowering activity of Compound 1, whereas the low affinity site is irrelevant to Aβ lowering. Compound 3 competes with ³H-Compound 1 in binding to membranes obtained from 293 cells with a $K_i$ of 74.5 pM (n=2). At the low affinity Compound 1 site, Compound 3 competes with ³H-Compound 1 with a $K_i$ of 573.5 nM (n=2). Compound 3 inhibits Aβ production in 293 cells with an $IC_{50}$ of 585 pM. This value for whole cell biological activity of Compound 3 we attribute to its potency at the Aβ lowering, high affinity Compound 1 binding site, since the ratio of its Aβ lowering to the $K_i$ at the high affinity site is 7.9. For comparison, the ratio of the $K_i$ at the low affinity site to the $IC_{50}$ for Aβ lowering at the low affinity site is 980.3. This wide separation in high and low affinity $K_i$'s (7741.5; n=2) affords a wide window of concentrations of Compound 3 where binding of the compound is almost exclusively to the high affinity Compound 1 site.

SWE293 cells were successfully labelled with 5 nM of Compound 3 for flow cytometry analysis (excitation 488 nm, emission 510 (+/−10) nm) to give a four fold increase in fluorescence intensity over background unlabeled cells, consistent with the binding site being in relatively low abundance. At 5 nM concentration this compound only labels the high affinity Compound 1 (Aβ lowering) site. In the presence of 1 μM 5-(S)-[N'-((S)-3,5-Difluorophenyl-α-hydroxyacetyl)-L-alaninyl]amino-7-methyl-5,7-dihydro-6H-dibenz[b,d]azepin-6-one (Example 29), (which is sufficient to completely displace all specifically bound Compound of Example 28 at >>5 nM)), the signal was reduced by 20% (p<0.001), after background subtraction. Compound 3 is obviously a very hydrophobic molecule (log P>3), and the non displaceable signal is almost certainly due to non-specific partitioning into cell membranes.

Cells over-expressing the high affinity Compound 1 binding site are amenable to cell sorting after transfection of 293T cells with cDNA from a HEK 293 library. The strong induction of transcription with this vector system should result in a 50–100 fold increase in expression of the transfected gene. Thus, cells over-expressing the high affinity Compound 1 binding site are amenable to sorting by FACS, since at 5 nM, the non-displaceable binding will stay constant. The incorporated cDNA from positive cells is amplified, cloned and sequenced as a means to identify the protein mediating the functional γ-secretase inhibition.

From the foregoing description, various modifications and changes in the composition and method will occur to those skilled in the art. All such modifications coming within the scope of the appended claims are intended to be included therein.

What is claimed is:

1. An intermediate useful in the preparation of biological reagents that inhibit β-amyloid peptide release and/or its synthesis, wherein said intermediate is represented by formula VI $$A—B' \qquad\qquad VI$$

wherein A is represented by formula V

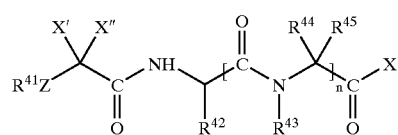

wherein $R^{41}$ is selected from the group consisting of alkyl, alkenyl, alkynyl, cycloalkyl, cycloalkenyl, substituted alkyl, substituted alkenyl, substituted alkynyl, aryl, heteroaryl and heterocyclic;

$R^{42}$ is selected from the group consisting of hydrogen, alkyl, substituted alkyl, alkenyl, substituted alkenyl, alkynyl, substituted alkynyl, cycloalkyl, aryl, heteroaryl and heterocyclic;

each $R^{43}$ is independently selected from the group consisting of hydrogen and methyl and $R^{43}$ together with $R^{44}$ can be fused to form a cyclic structure of from 3 to 8 atoms which is optionally fused with an aryl or heteroaryl group;

each $R^{44}$ is independently selected from the group consisting of hydrogen, alkyl, alkenyl, alkynyl, aryl, cycloalkyl, cycloalkenyl, heteroaryl, heterocyclic, substituted alkyl, substituted alkenyl and substituted alkynyl;

each $R^{45}$ is selected from hydrogen and methyl or together with $R^{43}$ forms a cycloalkyl group of from 3 to 6 carbon atoms;

X is selected from oxygen, sulfur and NH;

X' is hydrogen, hydroxy or fluoro; and

X" is hydrogen, hydroxy or fluoro, or X' and X" together form an oxo group;

Z is selected from the group consisting of a bond covalently linking $R^{41}$ to —CX'X"—, oxygen and sulfur;

n is an integer equal to 1 to 3; and

B' is selected from the group consisting of
 a) $(CH_2CH(R)Q)_nH$
 b) alkylene-Q—H
 c) substituted alkylene-Q—H wherein R is selected from hydrogen, alkyl or aryl and Q is selected from the group consisting of —O—, —S— and —NH—.

2. A compound selected from the group consisting of:

8-N'((2-(R/S)-hydroxy-2-(3,5-difluorophenyl)-acetyl-L-alaninyl)-L-phenylglycinyl)amino-3,6-dioxaoctyl-amine hydrochloride;

Methyl N-[2-N-((2-(R/S)-hydroxy-2-(3,5-difluorophenyl)-acetyl-L-alaninyl)-L-phenylglycinyl)aminoethyl]-N'-2-aminoethyl amine hydrochloride;

2-N'-((2-(R/S)-hydroxy-2-(3,5-difluorophenyl)-acetyl-L-alaninyl)-L-phenylglycine)-ethylamine hydrochloride; and 2-(2'-(N'(((R/S)-3,5-difluorophenyl-α-hydroxyacetyl)-L-alanine)-L-phenylglycine)aminoethoxy)ethylamine, hydrochloride salt.

* * * * *

SEQUENCE LISTING

```
<160> NUMBER OF SEQ ID NOS:   1

<210> SEQ ID NO 1
<211> LENGTH: 43
<212> TYPE: PRT
<213> ORGANISM: beta-amyloid precursor protein

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
        35                  40
```